(12) United States Patent
Schumann et al.

(10) Patent No.: US 12,076,300 B2
(45) Date of Patent: *Sep. 3, 2024

(54) DOSAGE REGIME WITH ESKETAMINE FOR TREATING MAJOR DEPRESSIVE DISORDER

(71) Applicant: CLEXIO BIOSCIENCES LTD., Jerusalem (IL)

(72) Inventors: Johanna Schumann, Jerusalem (IL); Dorit Mimrod, Jerusalem (IL)

(73) Assignee: CLEXIO BIOSCIENCES LTD., Petach Tikva (IL)

(*) Notice: Subject to any disclaimer, the term of this patent is extended or adjusted under 35 U.S.C. 154(b) by 18 days.

This patent is subject to a terminal disclaimer.

(21) Appl. No.: 18/193,083

(22) Filed: Mar. 30, 2023

(65) Prior Publication Data

US 2023/0248666 A1 Aug. 10, 2023

Related U.S. Application Data

(63) Continuation of application No. 17/789,631, filed as application No. PCT/IB2020/062507 on Dec. 29, 2020.

(60) Provisional application No. 62/954,779, filed on Dec. 30, 2019.

(51) Int. Cl.
| | |
|---|---|
| *A61K 31/135* | (2006.01) |
| *A61K 31/137* | (2006.01) |
| *A61K 31/138* | (2006.01) |
| *A61K 31/15* | (2006.01) |
| *A61K 31/343* | (2006.01) |
| *A61K 31/381* | (2006.01) |
| *A61K 31/4525* | (2006.01) |
| *A61K 45/06* | (2006.01) |
| *A61P 25/24* | (2006.01) |

(52) U.S. Cl.
CPC .......... *A61K 31/135* (2013.01); *A61K 31/137* (2013.01); *A61K 31/138* (2013.01); *A61K 31/15* (2013.01); *A61K 31/343* (2013.01); *A61K 31/381* (2013.01); *A61K 31/4525* (2013.01); *A61K 45/06* (2013.01); *A61P 25/24* (2018.01)

(58) Field of Classification Search
CPC .... A61K 31/135; C07C 2225/20; A61P 25/24
See application file for complete search history.

(56) References Cited

U.S. PATENT DOCUMENTS

| | | | |
|---|---|---|---|
| 7,955,619 B2 | 6/2011 | Shah et al. | |
| 9,468,611 B2 | 10/2016 | Manfredi et al. | |
| 10,478,405 B2 | 11/2019 | Charney et al. | |
| 11,253,487 B2* | 2/2022 | Kagan | A61K 9/1652 |
| 2004/0052731 A1 | 3/2004 | Hirsh et al. | |
| 2013/0236573 A1 | 9/2013 | Singh et al. | |
| 2015/0359759 A1 | 12/2015 | Katz | |
| 2016/0332962 A1 | 11/2016 | Chen et al. | |
| 2016/0338977 A1 | 11/2016 | Singh et al. | |
| 2018/0256534 A1 | 9/2018 | Erickson | |
| 2018/0325844 A1 | 11/2018 | Brachman et al. | |
| 2020/0000748 A1 | 1/2020 | Kagan et al. | |
| 2020/0147005 A1 | 5/2020 | Kagan et al. | |
| 2021/0386688 A1 | 12/2021 | Canuso et al. | |
| 2022/0125742 A1 | 4/2022 | Kagan et al. | |
| 2023/0063459 A1 | 3/2023 | Schumann et al. | |

FOREIGN PATENT DOCUMENTS

| | | | |
|---|---|---|---|
| CN | 101466364 A | 6/2009 | |
| CN | 107735081 A | 2/2018 | |
| DE | 2062620 A1 | 7/1971 | |
| DE | 102007009888 A1 | 9/2008 | |
| EA | 020339 B1 | 10/2014 | |
| GB | 1330878 A | 9/1973 | |
| JP | 2018-515557 A | 6/2018 | |
| WO | 2007/111880 A2 | 10/2007 | |
| WO | 2008/023261 A1 | 2/2008 | |
| WO | 2008/033523 A1 | 3/2008 | |
| WO | 2011/020061 A2 | 2/2011 | |
| WO | 2013/138322 A1 | 9/2013 | |
| WO | 2014/006004 A1 | 1/2014 | |
| WO | 2014/020155 A1 | 2/2014 | |
| WO | 2015/031410 A1 | 3/2015 | |
| WO | 2015/051259 A1 | 4/2015 | |
| WO | 2015/066172 A1 | 5/2015 | |
| WO | 2015/158854 A1 | 10/2015 | |
| WO | 2016/044150 A1 | 3/2016 | |
| WO | 2016/073653 A1 | 5/2016 | |
| WO | 2016/094358 A1 | 6/2016 | |
| WO | 2016/187491 A1 | 11/2016 | |
| WO | 2017/041112 A1 | 3/2017 | |
| WO | 2018/079693 A1 | 5/2018 | |
| WO | 2018/102488 A1 | 6/2018 | |
| WO | 2018/234568 A2 | 12/2018 | |
| WO | WO 2019/073408 * | 4/2019 | ........... C07C 225/20 |
| WO | 2019/126108 A1 | 6/2019 | |
| WO | 2020/003195 A1 | 1/2020 | |

(Continued)

OTHER PUBLICATIONS

Segmiller et al. The Journal of Clinical Pharmacology 2013, 53 (9), 996-998.*
Peltoniemi et al. Clin Pharmacokinet 2016, 55, 1059-1077.*
Cusin et al. Rating Scales for Depression, Handbook of Clinical Rating Scales and Assessment in Psychiatry and Mental Health, L. Baer, M.A. Blais (Eds.), Humana Press, 2010, Chapter 2, pp. 7-35.*
Co-pending U.S. Appl. No. 18/193,055, effective filing date Mar. 30, 2023.*
Co-pending U.S. Appl. No. 17/789,631, effective filing date Jun. 28, 2022.*
Co-pending U.S. Appl. No. 16/592,930, effective filing date Oct. 4, 2019.*
Co-pending U.S. Appl. No. 17/571,731, effective filing date Jan. 10, 2022.*
Co-pending U.S. Appl. No. 18/193,122, effective filing date Mar. 30, 2023.*
Co-pending U.S. Appl. No. 16/454,399, effective filing date Jun. 27, 2019.*

(Continued)

*Primary Examiner* — Irina Neagu
(74) *Attorney, Agent, or Firm* — BakerHostetler

(57) ABSTRACT

The present disclosure provides methods for safe and efficacious administration of esketamine.

5 Claims, No Drawings

(56) References Cited

FOREIGN PATENT DOCUMENTS

| WO | 2020/225773 A1 | 11/2020 |
|---|---|---|
| WO | 2021/026232 A1 | 2/2021 |
| WO | 2021/116498 A1 | 6/2021 |

OTHER PUBLICATIONS

Striebel et al., "(Being with a Buddha): A Case Report of Methoxetamine Use in a United States Veteran with PTSD' Case Reports", Psychiatry, 2017, Article ID 2319094, pp. 1-5.
Thomas et al., "Rapid effectiveness of intravenous ketamine for ultraresistant depression in a clinical setting and evidence for baseline anhedonia and bipolarity as clinical predictors of effectiveness", J Psychopharmacology, 2018, vol. 32, No. 10, pp. 1110-1117.
Toyama et al., "Genotoxic Effects of N-nitrosoketamine and Ketamine as Assessed by In Vitro Micronucleus Test in Chinese Hamster Lung Fibroblast Cell Line", Environ. Health Prev. Med., May 2006, vol. 11, pp. 120-127.
Vallesenor et al., "A pilot study of plasma metabolomic patterns from patients treated with ketamine for bipolar depression: evidence for a response-related difference in mitochondrial networks", Br J Pharmacology, 2014, vol. 171, pp. 2230-2242.
Van de Loo, et al., "The effects of intranasal esketamine (84 mg) and oral mirtazapine (30 mg) on on-road driving performance: a double-blind, placebo-controlled study", Psychopharmacology, 2017, vol. 234, pp. 3175-3183.
Vesierra Label, Jan. 2018, 12 pages.
Wallace et al: Randomized, double-blind, placebo-controlled, dose-escalation study: Investigation of the safety, pharmacokinetics, and antihyperalgesic activity of l-4-chlorokynurenine in healthy volunteer, Scandinavian Journal of Pain, 2017, vol. 17, pp. 243-251.
Wasteson et al., "Depression assessment and classification in palliative cancer patients: a systematic literature review", Palliative Medicine, 2009, vol. 23, No. 8, pp. 739-753.
White et al., "Comparative Pharmacology of the Ketamine Isomers", Brit. Journal Anaesth., 1985, vol. 57, pp. 197-203.
White, et al., "Pharmacology of Ketamine Isomers in Surgical Patients", Anesthesiology, 1980, vol. 52, pp. 231-239.
Wilkinson et al., "A Survey of the Clinical, Off-Label Use of Ketamine as a Treatment for Psychiatric Disorders", Am. J. Psychiatry, Jul. 2017, vol. 174, No. 7, pp. 695-696.
Witkin Jeffrey M et al: "Rapid-Acting Antidepressants", Current Pharmaceutical Design, vol. 24, No. 22, Jun. 2018, pp. 2556-2563.
Womble, "Effects of Ketamine on Major Depressive Disorder in a Patient With Posttraumatic Stress Disorder", AANA Journal, Apr. 2013, vol. 81, No. 2, pp. 118-119.
Yanagihara et al., "Plasma Concentration Profiles of Ketamine and Norketamine After Administration of Various Ketamine Preparations to Healthy Japanese Volunteers", Biopharmaceutics & Drug Disposition, 2003, vol. 24, No. 1, pp. 37-43.
Yang et al., "R-ketamine: A Rapid-Onset and Sustained Antidepressant Without Psychotomimetic Side Effects", Transl. Psychiatry, Sep. 2015, 11 pages.
Yehuda et al., "What I have changed my mind about and why", European Journal of Psychotraumatology, 2016, vol. 7, pp. 1-9.
Zanos Panos, et al: "Ketamine and Ketamine Metabolite Pharmacology: Insights into Therapeutic Mechanisms", Pharmacological Reviews, vol. 70, No. 3, Jun. 2018, pp. 621-660.
Zarate et al., "Replication of Ketamine's Antidepressant Efficacy in Bipolar Depression: A Randomized Controlled Add-on Trial", Biol. Psychiatry., 2012, vol. 71, No. 11, pp. 939-946.
Zhang et al., "R(-)-ketamine Shows Greater Potency and Longer Lasting Antidepressant Effects Than S (+)-ketamine" Pharmacology, Biochemistry and Behavior, Jan. 2014, vol. 116, pp. 137-141.
Zhao et al., Simultaneous population pharmacokinetic modelling of ketamine and three major metabolites in patients with treatment-resistant bipolar depression, BJCP, 2012, vol. 74, No. 2, pp. 304-314.
Zigmond et al., "The Hospital Anxiety and Depression Scale", 1983, vol. 67, pp. 361-370.
Zulresso FDA Label, Full Prescribing Information, Sep. 30, 2019, 21 pages.
"OxyContin® (oxycodone hydrochloride controlled-release) Tablets, for oral use, CII," Highlights of Prescribing Information, Reference ID: 3155030, Jul. 2012, pp. 1-31.
2019 FDA Esketamine Briefing Document, Esketamine Nasal Spray for Patients with Treatment-resistant Depression, Janssen Research & Development, LLC, Feb. 8, 2019, pp. 1-260.
Adhvaryu et al., "Genotoxic Effects of Ketamine on CHO Cells", Arch. Toxicology, 1986, vol. 59, pp. 124-125.
Alberich et al 'Efficacy and safety of ketamine in bipolar depression : A systematic review' Rev Psiquiatr Salud Ment (Bare.), May 2017; vol. 10(2), pp. 104-112.
Albott et al., "Efficacy, safety and durability of repeated ketamine infusions for comorbid posttraumatic stress disorder and treatment depression", J. Clin. Psychiatry, 2018, vol. 79(3), 11634, pp. 8.
Allergan Study For NCT03726658, AGN-241751 in the Treatment of Major Depressive Disorder, Last Updated on Oct. 8, 2019.
Angst et al, Differential psychopathology and patterns of cerebral glucose utilisation produced by (S)- and (R)-ketamine in healthy volunteers using positron emission tomography (PET), European Neuropsychopharmacology 7, Jul. 1997, pp. 25-38.
Anonymous: "Trial NL6030 (NTR6161) Ketaminestudie", Netherlands Trial register Oct. 21, 2016 (Oct. 21, 2016), pp. 1-6, XP002796356, Retrieved from the Internet: URL:https://www.trialregister.nl/trial/6030.
APA Annual Meeting Poster P7-065, Mar. 18, 2018.
APA Annual Meeting Poster P8-054, Mar. 18, 2018.
Arabzadeh, et al., Journal of Affective Disorders, Does oral administration of ketamine accelerate response to treatment in major depressive disorder? Results of a double-blind controlled trial, Journal of Affective Disorders, https://doi.org/10.1016/j.jad.2018.02.056, 26 pages, Feb. 2018, pp. 236-241.
ASCP Annual Meeting Poster T67, May 29, 2018.
ASCP Annual Meeting Poster W68, May 29, 2018.
Averill et al., "Glutamate dysregulation and glutamatergic therapeutics for PTSD: Evidence from human studies", Neuroscience Letters, 2017, vol. 649, pp. 147-155.
Avinza® (morphine sulfate) extended-release capsules, for oral use, CII, Highlights of Prescribing Information, Reference ID: 3155722, Jul. 2012, pp. 1-18.
Banwani et al., "Ketamine-induced affective switch in a patient with treatment-resistant depression", Indian J Pharmacol., 2015, vol. 47, No. 4, pp. 454-455.
Berman et al., "Antidepressant Effects of Ketamine in Depressed Patients", Biol. Psychiatry, 2000, pp. 351-354.
Bioequivalence Studies with Pharmacokinetic Endpoints for Drugs Submitted Under and ANDA Guidance for Industry, Aug. 2021.
Blonk et al., "Use of Oral Ketamine in Chronic Pain Management: A Review", European Journal of Pain, 2010, pp. 466-472.
Bobo et al 'Ketamine for treatment-resistant unipolar and bipolar major depression: critical review and implications for clinical practice' Depression and Anxiety, 2016, vol. 33, pp. 698-710.
Body Weight at www.cnn.com/2018/12/20/health/us-average-height-weight-report/index.html (retrieved from the internet Aug. 25, 2021) (Year: 2018).
Branerjee et al, "AGN-241751, an Orally Bioavailable Positive NMDA Receptor Modulator, Exhibits Rapid and Sustained Antidepressant-Like Effects in Rodents", Biological Psychiatry, May 15, 2019, vol. 85, S348.
Brennan et al., "The comparative pharmacokinetics of physical manipulation by crushing of XtampzaR ER compared with OxyContin", Future Medicine Ltd., Sep. 18, 2017, 12 pages.
Calabrese et al 'A Randomized, Double-Blind, Placebo-Controlled Trial of Quetiapine in the Treatment of Bipolar 1 or II Depression' Am J Psychiatry 2005, vol. 162, pp. 1351-1360.
Canuso et al., "Efficacy and Safety of Intranasal Esketamine for the Rapid Reduction of Symptoms of Depression and Suicidality in Patients at Imminent Risk for Suicide: Results of a Double-Blind, Randomized, Placebo-Controlled Study", The American Journal of Psychiatry, Jul. 2018, vol. 175, No. 7, pp. 620-630.

(56) References Cited

OTHER PUBLICATIONS

Celon Pharma Press Release, Celon Pharma S.A. begins a clinical programme for Esketamine in the treatment of drug-resistant depression, Nov. 28, 2017.
Celon Pharma Press Release, Completed administration of the Esketamine-based drug to all subjects of the first part of the phase 1 trial; Jan. 5, 2018.
Chedekel, Yale, "Magic Antidepressant May Hold promise for PTSD", Harvard Courant, Jun. 3, 2012.
Chen et al, "Therapeutic effects of add-on low-dose dextromethorphan plus valproic acid in bipolar disorder", European Neuropsychopharmacology, Sep. 2014, vol. 24, pp. 1753-1759.
Chong et al., "Development of a Sublingual/Oral Formulation of Ketamine for Use in Neuropathic Pain", Clin Drug Invest 2009, vol. 29, No. 5, pp. 317-324.
Clements et al., "Bioavailability, Pharmacokinetics and Analgesic Activity of Ketamine in Humans", Journal of Pharmaceutical Sciences, May 1982, pp. 539-542.
Correia-Melo et al 'Rapid infusion of esketamine for unipolar and bipolar depression: a retrospective chart review' Neuropsychiatric Disease and Treatment 2017:13 1627-1632.
Cortef Product Label, Nov. 1993, 2 pages.
Currie, "Pharmacology, Part 1: Introduction to Pharmacology and Pharmacodynamics," Journal of Nuclear Medicine Technology, vol. 46, No. 2, Jun. 2018, pp. 81-86.
D'Andrea et al., "Transient Resolution of Treatment-Resistant Posttraumatic Stress Disorder Following Ketamine Infusion", Biol Psy, 2013, vol. 74, pp. e-13-e14.
Dahan et al., "Population pharmacokinetic-pharmacodynamic modeling of ketamine-induced pain relief of chronic pain", European Journal of Pain, vol. 15, 2011, pp. 258-267.
Daly et al., "A Randomized Withdrawal, Double-Blind, Multicenter Study of Esketamine Nasal Spray Plus an Oral Antidepressant for Relapse Prevention in Treatment-Resistant Depression", Presented at the 2018 Annual Meeting of the American Society of Clinical Psychopharmacology (ASCP), May 30, 2018, 1 page.
Daly et al., "Efficacy and Safety of Intranasal Esketamine Adjunctive to Oral Antidepressant Therapy in Treatment-Resistant Depression: A Randomized Clinical Trial," JAMA Psychiatry, 2018, vol. 75, No. 2, pp. 139-148.
Daly et al., "Intranasal Esketamine in Treatment-resistant Depression, a Dose Response Study—Double Blind and Open Label Extension Data", Neuropsychopharmacology, 2015, vol. 40, pp. 5272-5442.
Diazgranados et al., "A Randomized Add-on Trial of an N-methyl-D-aspartate Antagonist in Treatment-Resistant Bipolar Depression", Arch Gen Psychiatry. Aug. 2010, vol. 67, No. 8, pp. 793-802.
Domino, "Taming the Ketamine Tiger", Anesthesiology, 2010, vol. 113, pp. 678-686.
Donoghue et al., "Remission From Behavioral Dysregulation in a Child With PTSD After Receiving Procedural Ketamine", Pediatrics, 2015, vol. 136, e694.
DSM-V "Major Depressive Disorder", 2013, at p. 161.
Durgam et al., "An 8-Week Randomized, Double-Blind , Placebo-Controlled Evaluation of the Safety and Efficacy of Cariprazine in Patients With Bipolar 1 Depression", Am J Psychiatry 2016, vol. 173, No. 271-281.
Earley et al., "Cariprazine Treatment of Bipolar Depression: A Randomized Double-Blind Placebo-Controlled Phase 3 Study", Am J Psychiatry, Jun. 2019, vol. 176, No. 6, pp. 439-448.
Ebert et al., "Norketamine, The Main Metabolite of Ketamine, is a non-competitive NMDA Receptor Antagonist in the Rat Cortex and Spinal Cord", European Journal of Pharmacology, 1997, vol. 333, pp. 99-104.
EMCDDA, Report on the Risk Assessment of Ketamine in the Framework of the Joint Action on New Synthetic Drugs, 2002, 120 pages.
European Monitoring Centre for Drug and Drug Addition's 2002 risk assessment report of Ketamine, p. 49-50.
Fanta et al., "Population Pharmacokinetics of S-ketamine and Norketamine in Healthy Volunteers After Intravenous and Oral Dosing", Eur. J. Clin. Pharmacol., Mar. 1, 2015, vol. 71, No. 4, pp. 441-447.
Fava et al: "Opioid Modulation With Buprenorphine/Samidorphan as Adjunctive Treatment for Inadequate Response to Antidepressants: A Randomized Double-Blind Placebo-Controlled Trial", Am. J. Psychiatry, May 2016, vol. 173, pp. 499-508.
Fava, et al., "Major Depressive Disorder", Neuron, Nov. 2000, vol. 28, pp. 335-341.
Feder et al., "Efficacy of Intravenous Ketamine for Treatment of Chronic Posttraumatic Stress Disorder", JAMA Psychiatry, 2014, vol. 71, No. 6, pp. 681-688.
Geisslinger et al., "Pharmacokinetics and Pharmacodynamics of Ketamine Enantiomers in Surgical Patients Using a Stereoselective Analytical Method", British Journal of Anesthesia, 1993, vol. 70, pp. 666-671.
Giorgetti, et al., "Effects of ketamine on psychomotor, sensory and cognitive functions relevant for driving ability", Forensic Science International, 2015, vol. 252, pp. 127-142.
Grady et al1 Ketamine for the treatment of major depressive disorder and bipolar depression: A review of the literature1 Ment Health Clin [Internet], 2017, vol. 7, No. 1, pp. 16-23.
Grant et al., "Pharmacokinetics and Analgesic Effects of I.M. and Oral Ketamine", British Journal of Anesthesia, 1981, vol. 53, pp. 805-810.
Hagelberg et al., "Clarithromycin, a potent inhibitor of CYP3A, Greatly Increases Exposure to Oral S-ketamine", European Journal of Pain, 2010, pp. 625-629.
Han et al: "Oral scopolamine augmentation for major depression", Expert Rev. Neurother, 2013, vol. 13, No. 1, pp. 19-21.
Hartberg, et al., Psychopharmacology, Impact of oral ketamine augmentation on hospital admissions in treatment-resistant depression and PTSD: a retrospective study, 2018, pp. 393-398.
Hartvig et al., "Central Nervous System Effects of Subdissociative Doses of (S)-ketamine are Related to Plasma and Brain Concentrations Measured with Positron Emission Tomography in Healthy Volunteers", Clin. Pharm. & Then, 1995, vol. 58, No. 2, pp. 165-173.
Hashimoto et al., "R-ketamine: A Rapid-Onset and Sustained Antidepressant Without Risk of Brain Toxicity", Psychological Medicine, Aug. 2016, vol. 46, pp. 2449-2451.
Hasin et al., "Epidemiology of Major Depressive Disorder", Arch. Gen. Psychiatry, 2005, vol. 62, pp. 1097-1106.
Himmelseher et al., "Ketamine for Perioperative Pain Management", Anesthesiology, Jan. 2005, vol. 102, pp. 211-220.
Hintzsche, "Subanesthetic-Dose Ketamine to Decrease Emergence Delirium in the Surgical Patient With Posttraumatic Stress Disorder", AANA Journal, Jun. 2018, vol. 86, No. 3, pp. 220-224.
Horn et al., "Understanding resilience: New approaches for preventing and treating PTSD", Experimental Neurology, 2016, vol. 284, pp. 119-132.
Hou et al., "Applying ketamine to alleviate the PTSD-like effects by regulating the HCNI-related BDNF", Progress in Neuropsychopharmacology & Biological Psychiatry, 2018, vol. 86, pp. 313-321.
Huge et al., "Effects of low-dose intranasal (S)-ketamine in patients with Neuropathic pain", European Journal of Pain, 2010, pp. 387-394.
Ihmsen et al, "Stereoselective pharmacokinetics of ketamine: R(−)-Ketamine inhibits the elimination of S(+)-ketamine", Clinical Pharmacology & Therapeutics, 2001, vol. 70, pp. 431-438.
Irwin et al., "Daily Oral Ketamine for the Treatment of Depression and Anxiety in Patients Receiving Hospice Care: A 28-Day Open-Label Proof-of-Concept Trail", Journal of Palliative Medicine, 2013, vol. 16, No. 8, pp. 958-965.
Jafarinia, et al., Journal of Affective Disorders, Efficacy and safety of oral ketamine versus diclofenac to alleviate mild to moderate depression in chronic pain patients: A double-blind, randomized, controlled trial 204, 2016, pp. 1-8.
Janssen Announces Results of Esketamine Nasal Spray Phase 3 Study in Patients with Treatment-Resistant Depression, Innovation, Sep. 21, 2018, 6 pages.

(56) References Cited

OTHER PUBLICATIONS

Janssen Study For NCT03808259, A Study to Investigate the Different Modes of (S) Ketamine Administration in Healthy Participants, Last Updated Sep. 12, 2019.
Janssen Submits Esketamine Nasal Spray New Drug Application to U.S. FDA for Treatment-Resistant Depression, Sep. 4, 2018 [Retrieved from internet https://www.prnewswire.com/news-releases/janssen-submits-esketamine-nasal-spray-new-drug-application-to-us-fda-for-treatment-resistant-depression-300705975.html], 6 pages.
Jarventausta et al., "S-ketamine for the Treatment of Depression", Psychiatria Fennica, 2015, vol. 46, pp. 11-20.
Kelley et al., "Open-Label Placebo for Major Depressive Disorder: A Pilot Randomized Controlled Trial," Psychotherapy and Psychosomatics, vol. 81, No. 5, Aug. 2012, pp. 1-4.
Kelmendi et al., "PTSD: from neurobiology to pharmacological treatments", European Journal of Psychotraumatology, 2016, vol. 7, 31858, pp. 1-11.
Ketamine as a Rapid Treatment for Post-Traumatic Stress Disorder, Grant No. W81XWH-08-1-0602, U.S. Army Medical Research and Material Command, Oct. 2011.
Ketamine INN, Update Review Report Agenda Item 6.1, Expert Committee on Drug Dependence, WHO, 37th Meeting, Geneva, Nov. 2015, pp. 1-46.
Kharasch et al., "Metabolism of Ketamine Stereoisomers by Human Liver Microsomes", Anesthesiology, 1992, vol. 77, pp. 1201-1207.
Kim, "Ketamine for Treatment-Resistant Depression or Post-Traumatic Stress Disorder in Various Settings: A Review of Clinical Effectiveness, Safety, and Guidelines", CADTH Rapid Response Report, Mar. 2017, pp. 1-30.
Kishimoto et al., Compliance and persistence with daily, weekly, and monthly bisphosphonates for osteoporosis in Japan: analysis of data from the CISA, Arch Osteoporos, 2015, vol. 10, No. 27, pp. 1-6.
Kraus et al 'Administration of ketamine for unipolar and bipolar depression' Int J Psychiatry Clin Pract. Mar. 2017, vol. 21, No. 1, pp. 2-12.
Krystal et al., "Synaptic Loss and the Pathophysiology of PTSD: Implications for Ketamine as a Prototype Novel Therapeutic", Curr. Psychiatry, Rep., Apr. 2018, vol. 19, No. 10, 74, pp. 20.
Lara et al., "Antidepressant, mood stabilizing and procognitive effects of very low dose sublingual ketamine in refractory unipolar and bipolar depression", International Journal of Neuropsychopharmacology, 2013, vol. 16, pp. 2111-2117.
Lloyd-Williams et al., "A pilotrandomisedcontrolledtrialtoreduces ufferingandemotional distress in patients with advanced cancer", J Affect Dis 2013, vol. 148, pp. 141-145.
Lloyd-Williams et al., "Antidepressant medication in patients with advanced cancer—an observational study", QJM, Nov. 2013, vol. 106, No. 11, pp. 995-1001.
Loebel et al., "Lurasidone Monotherapy in the Treatment of Bipolar 1 Depression: A Randomized,Double-Blind, Placebo-Controlled Study", Am J Psychiatry, 2014, vol. 171, pp. 160-168.
Ionescu et al 'A single infusion of ketamine improves depression scores in patients with anxious bipolar depression' Bipolar Disord. Jun. 2015, vol. 17, No. 4, pp. 438-443.
Major Depressive Disorder: Developing Drugs for Treatment Guidance for Industry; U.S. Dept. of Health and Human Services Food and Drug Administration;—Center for Drug Evaluation and Research; Revision 1; Jun. 2018; 11 pages.
Malinosky et al., "Ketamine and Norketamine Plasma Concentrations after i.v., Nasal and Rectal Administration in Children", British Journal of Anaesthesia, 1996, vol. 22, pp. 203-207.
Marcus, S.C. et al., Antipsychotic Adherence and Rehospitalization in Schizophrenia Patients Receiving Oral Versus Long-Acting Injectable Antipsychotics Following Hospital Discharge, JMCP, Sep. 2015, vol. 21, No. 9, pp. 764.
Mathew et al., "Ketamine for Treatment-Resistant Unipolar Depression: Current Evidence", CNS Drugs, Mar. 1, 2012, vol. 26, No. 3, pp. 189-204.

McGhee et al., "The correlation between ketamine and post-traumatic stress disorder in burned service members", The Journal of Trauma: Injury, Infection and Critical Care, Feb. 2008, vol. 64, Issue 2, pages S195-S199.
Mikics et al., "The role of GluN2B-containing NMDA receptors in short- and long-term fear recall", Physiology & Behavior, 2017, vol. 177, pp. 44-48.
Mion et al., "A retrospective study of ketamine administration and the development of acute or post-traumatic stress disorder in 274 war-wounded soldiers", Anaesthesia, 2017, vol. 72, pp. 1476-1483.
Molero et al., "Antidepressant Efficacy and Tolerability of Ketamine and Esketamine: A Critical Review", CNS Drugs, May 2018, 10 pages.
Morrison, "Effect of intranasal esketamine on cognitive functioning in healthy participants: a randomized, double-blind, placebo-controlled study", Psychopharmacology, Feb. 2018, vol. 235, pp. 1107-1119.
Mrazek et al., "A Review of the Clinical, Economic, and Societal Burden of Treatment-Resistant Depression: 1996-2013", Psychiatric Services, Aug. 2014, vol. 65, No. 8, pp. 977-987.
Musazzi et al., "What Acute Stress Protocols Can Tell Us About PTSD and Stress-Related Neuropsychiatric Disorders", Frontiers in Pharmacology, Jul. 2018, vol. 9, Article 758.
NCT01998958, Oct. 29, 2015.
NCT02133001, Mar. 18, 2016.
NCT02343289, Jan. 21, 2015.
NCT02417064, Apr. 10, 2015.
NCT02418585, Apr. 13, 2015.
NCT02422186, Apr. 16, 2015.
NCT02493868, Jul. 7, 2015.
NCT02497287, Jun. 10, 2015.
NCT02782104, May 25, 2016.
NCT02918318, Sep. 27, 2016.
NCT03039192, Feb. 1, 2017.
NCT03097133, Mar. 27, 2017.
NCT03185819, Jun. 12, 2017.
NCT03434041, Feb. 18, 2018.
NCT03965871 trial protocol as accessed Jul. 25, 2019.
Netherlands Pharmacovigilance Centre report, Esketamine and hepatotoxicity, May 2013, 7 pages.
Noppers et al., "Drug-induced liver injury following a repeated course of ketamine treatment for chronic pain in CRPS type 1 patients: A report of 3 cases"., Pain, vol. 152, 2011, pp. 2179-2178.
Norrholm et al., "Fear Extinction in Traumatized Civilians with Posttraumatic Stress Disorder: Relation to Symptom Severity", Biol Psychiatry, 2011, pp. 69556-69563.
Nugent et al., "Neural correlates of rapid antidepressant response to ketamine in bipolar disorder", Bipolar Disord. Mar. 2014, vol. 16, No. 2, pp. 119-128.
Och-Ross et al., "Efficacy and Safety of Intranasal Esketamine Plus and Oral Antidepressant in Elderly Patients with Treatment-Resistant Depression", 2018 Annual Meeting of the American Psychiatric Association (APA), May 8, 2018, 2 pages.
Ostuzzi et al., "Cochrane Database of Systematic Reviews, Antidepressants for the treatment of depression in people with cancer (Review)", 2018, pp. 1-78.
Oye et al., "Effects of Ketamine on Sensory Perception: Evidence for a Role of N-Methyl-D-Aspartate Receptors", Journal of Pharmacology and Experimental Therapeutics, Mar. 1992, vol. 260, No. 3, pp. 1209-1213.
Papakostas et al., "The Nature of Placebo Response in Clinical Studies of Major Depressive Disorder", J. Clin. Psychiatry, 2015, vol. 76, No. 4, pp. 456-466.
Paslakis et al., "Oral Administration of the NMDA Receptor Antagonist S-Ketamine as Add-On Therapy of Depression: A Case Series", Pharmacopsychiatry, Jan. 2010, vol. 43, No. 1, pp. 33-35.
Patent and Exclusivity for: N211243, Product 001, Esketamine Hydrochloride (Spravato) Spray EQ 28mg BASE, Orange Book: Approved Drug Products with Therapeutic Equivalence Evaluations, [Retrieved from internet on Apr. 4, 2023 https://www.accessdata.fda.gov/scripts/cder/ob/patent_info.cfm?Product_No=001&Appl_No=211243&Appl_type=N], 2 pages.

(56) References Cited

OTHER PUBLICATIONS

Peltoniemi et al., "Ketamine: A Review of Clinical Pharmacokinetics and Pharmacodynamics in Anesthesia and Pain Therapy", Clin Pharmacokinet 2016, vol. 55, pp. 1059-1077.

Peltoniemi et al., "Rifampicin has a Profound Effect on the Pharmacokinetics of Oral S-Ketamine and Less on Intravenous S-Ketamine", Basic & Clinical Pharmacology, 2012, vol. 111, pp. 325-332.

Peltoniemi et al., "S-ketamine concentrations are greatly increased by grapefruit juice," European Journal of Clinical Pharmacology, vol. 68, No. 6, Jan. 2012, pp. 979-986.

Pfenninger et al., "Cognitive Impairment after Small-dose Ketamine Isomers in Comparison to Equianalgesic Racemic Ketamine in Human Volunteers", Anesthesiology, 2002, vol. 96, pp. 357-366.

Pradhan et al., "D-Serine is a potential biomarker for clinical response in treatment of posttraumatic stress disorder using (R,S)-ketamine infusion and Timber Psychotherapy: A Pilot Study", BBA—Proteins and Proteomics, 2018, vol. 1866, pp. 831-839.

Preskorn et al., "Randomized Proof of Concept Trial of GLYX-13, an N-Methyl-D-Aspartate Receptor Glycine Site Partial Agonist, in Major Depressive Disorder Nonresponsive to a Previous Antidepressant Agent", Journal of Psychiatric Practice, Mar. 2015, vol. 21, No. 2, pp. 140-149.

Qi et al., "Prevention of Post-Traumatic Stress Disorder After Trauma: Current Evidence and Future Directions", Curr Psychiatry Rep., 2016, vol. 18, pp. 1-11.

Rasmussen Feder et al., "Ketamine for Posttraumatic Stress Disorder", JAMA Psychiatry, Jan. 2015, vol. 72, No. 1, 2015, pp. 94-96.

Rayner et al., "Antidepressants for the treatment of depression in palliative care: systematic review and meta-analysis", Palliat Med., 2011, vol. 25, No. 1, pp. 36-51.

Reagan-Shaw, et al., Dose translation from animal to human studies revisited, The FASEB Journal, vol. 22, 2007, pp. 659-661.

Rong et al., "Predictors of Response to Ketamine in Treatment Resistant Major Depressive Disorder and Bipolar Disorder", Int. J. Environ. Res. Public Health, 2018, vol. 15, No. 771, pp. 1-10.

Rot et al., "Safety and Efficacy of Repeated-Dose Intravenous Ketamine for Treatment-Resistant Depression", Biol Psychiatry, 2010, vol. 67, pp. 139-145.

Sanacora, G. et al., A Consensus Statement on the Use of Ketamine in the Treatment of Mood Disorders, JAMA Psychiatry, Apr. 2017, vol. 74, No. 4, pp. 399-405.

Schoevers et al., "Oral Ketamine for the Treatment of Pain and Treatment-Resistant Depression",, British Journal of Psychiatry, 2016, vol. 208, pp. 108-113.

Schonenberg et al., "Effects of peritraumatic ketamine medication on early and sustained posttraumatic stress symptoms in moderately injured accident victims", Psychopharmacology, 2005, vol. 182, pp. 420-425.

Schonenberg et al., "Ketamine aggravates symptoms of acute stress disorder in a naturalistic sample of accident victims", Journal of Psychopharmacology, 2008, vol. 22, No. 5, pp. 493-497.

Segmiller, et al, Repeated S-ketamine Infusions in Therapy Resistant Depression: A Case Series; American College of Clinical Pharmacology, vol. 53, Issue 9, Sep. 2013, pp. 996-998.

Sharpe et al., "Major depression in outpatients attending a regional cancer centre: screening and unmet treatment needs", British Journal of Cancer, 2004, vol. 90, pp. 314-320.

Shirawi, et al., Journal of Clinical Psychopharmacology, Oral Ketamine in Treatment-Resistant Depression, vol. 37, No. 4, Aug. 2017, pp. 1-4, 464-467.

Shiroma et al., "Augmentation of response and remission to serial intravenous subanesthetic ketamine in treatment resistant depression", Journal of Affective Disorders, vol. 155, 2014, pp. 123-129.

Singh et al., "Intravenous Esketamine in Adult Treatment-Resistant Depression: A Double-Blind, Double-Randomization, Placebo-Controlled Study", Biological Psychiatry, 2016, vol. 80, pp. 424-431.

Smith-Apeldoorn et al., BMC Psychiatry; "Oral esketamine for treatment-resistant depression: rationale and design of a randomized controlled trial", BMC Psychiatry, vol. 19:375, No. 1, Nov. 2019, pp. 1-9.

Snaith et al., "The hospital anxiety and depression scale", 1986, vol. 292, 6516, p. 344.

Sofia et al., "Evaluation of Ketamine HCl for Anti-Depressant Activity", Arch. Int. Pharmacodyn. Ther., 1975, vol. 214, No. 1, pp. 68-74.

Spravato esketamine nasal spray, Approved Product Monograph, Canada, May 19, 2020, pp. 1-59.

Spravato Prescribing Information, Section 2.2, Mar. 2019.

* cited by examiner

DOSAGE REGIME WITH ESKETAMINE FOR TREATING MAJOR DEPRESSIVE DISORDER

CROSS-REFERENCE TO RELATED APPLICATIONS

This application is a continuation of U.S. application Ser. No. 17/789,631, filed Jun. 28, 2022, which is the National Stage Application of International Patent Application No. PCT/IB2020/062507, filed Dec. 29, 2020, which claims the benefit of priority to U.S. Provisional Application No. 62/954,779, filed Dec. 30, 2019, the entire contents of which are incorporated herein by reference.

FIELD OF THE INVENTION

The present disclosure provides methods for safe and efficacious administration of esketamine.

BACKGROUND OF THE INVENTION

Ketamine is a non-barbiturate, rapid acting, induction and general anesthetic agent that acts primarily via NMDA receptor antagonism in the CNS. The drug has been available in the United States since 1970 under the tradename Ketalar®. In 1971, DE2062620 described ketamine's (−) enantiomer, esketamine. Esketamine is not approved for use in the United States but is available in Europe as an induction and general anesthetic agent under the tradename Ketanest® S.

Sofia et al (1975) proposed the use of oral ketamine to treat depression. Berman et al (1980) described the results of a placebo controlled clinical trial of a single intravenous dose of ketamine in 7 patients with major depression. DE102007009888 suggests the use of (S)(+)-ketamine in the treatment of depression. More recently, there has been an increased interest in the possibility of using ketamine or esketamine for the treatment of major depressive disorder (MDD) including when the depression has proved refractory to other therapies.

Pharmaceutical compositions of ketamine and esketamine have been administered to healthy subjects and patients via a variety of roots of administration including intravenously, intranasally and orally. Clements et al (1982) record the relative bioavailability of oral ketamine as being 17% and of intramuscular ketamine as being 93%. Since that article, several other studies have recorded the relative oral bioavailability of ketamine as being between 17 and 24%. Malinovsky et al (1996) record the relative bioavailability of intranasal ketamine as being 50% and of rectal ketamine as being 30%. Yanagihara et al (2003) record the relative bioavailability of both rectal and sublingual ketamine as being 30%, whereas they found nasal bioavailability to be 45%.

Although esketamine has been available for more than 40 years, there is very little published literature into its relative bioavailability by non-intravenous routes. Peltoniemi et al (2012) record the oral bioavailability of esketamine as being 11%, whereas Fanta et al (2015) found it to be only 8% and suggest that the first-pass metabolism of esketamine is more extensive than that found with ketamine. Unfortunately, although the protocol of a study into the relative bioavailability of intranasal and oral esketamine, NCT02343289, was already described in 2015, no results have been published. Daly et al (2017) record that 56 mg and 84 mg administered intranasally produces plasma esketamine levels that are in the pharmacokinetic range achieved by an intravenous administration of 0.2 mg/kg of esketamine, suggesting that the relative bioavailability of intranasal esketamine might be considerably lower than that of ketamine.

The relative efficacy and safety of the two enantiomers of ketamine has also been a source of considerable debate in the literature. Ebert et al (1997) record that esketamine has a 5 times greater affinity for the NMDA receptor than (R)-ketamine. Oye et al (1992) record that esketamine was 4 times as potent as (R)-ketamine in reducing pain perception and in causing auditory and visual disturbances. Domino (2010) records that although esketamine appears more potent than (R)-ketamine, it also presents with greater undesirable psychotomimetic side effects. In contrast, Zhang et al (2014) and Yang et al (2015) have recorded that (R)-ketamine showed greater potency and longer-lasting antidepressant effects than esketamine in animal models of depression without psychotomimetic side effects and abuse liability. This has led some, such as Hashimoto (2016), to suggest that the anti-depressive effect of these molecules might not be due to NMDA receptor antagonism.

Despite the more recent interest in the use of ketamine and its enantiomers in the treatment of depression, most clinical reports describe the effects after a single administration. Blonk et al (2010) provide an extensive review of the doses recorded for chronic administration of oral ketamine in pain therapy and shows that typically high doses of 200 mg/d or more were prescribed for time periods of up to and greater than a year. Paslakis et al (2010) record four case reports of administering up to 1.25 mg/kg/d of oral esketamine as concomitant therapy in patients suffering from depression over a 14 day timeframe with two patients receiving up to 150 mg/d for 7 of their treatment days. Daly et al (2015) record the administration of 28 mg, 56 mg, and 84 mg of esketamine intranasally to patients twice a week for up to 14 days followed by an open label extension study of reduced dosing frequency for an additional 9 weeks, with all patients starting this extension on 56 mg/$2^{nd}$ week and most completing the study on 84 mg/$2^{nd}$ week.

U.S. patent application Ser. No. 16/592,930 details an efficacious method of treating major depressive disorder (MDD) by administering an oral dosage form of between about 5 mg and about 40 mg of esketamine over a treatment regimen of at least 28 days. Said application explains that for chronic therapy with an oral dosage form of esketamine, in order to preserve an, at least 10 fold, safety margin over the genotoxic findings presented, a maximum safe dose of 40 mg is allowable.

Surprisingly, it has now been found that chronic oral administration of doses of esketamine greater than 40 mg are safe and efficacious, without any increased risk of genotoxicity or mutagenicity.

SUMMARY OF THE INVENTION

In one embodiment, the invention relates to a method of treating major depressive disorder (MDD) in a human patient in need thereof comprising orally administering to said patient an oral dosage form comprising between about 41 mg and about 80 mg of esketamine over a treatment regimen of at least 28 days.

DETAILED DESCRIPTION OF THE INVENTION

The present invention is directed to methods of treating major depressive disorder in a human patient in need thereof comprising orally administering to said patient an oral dosage form comprising about 41 mg and about 80 mg (e.g., 41 mg to 80 mg) of esketamine over a treatment regimen of at least 28 days.

As used herein, the term "major depressive disorder", or MDD, is characterized as a psychiatric disorder meeting five criteria: 1) the presence during the same 2 week period which together represent a change from previous functioning, of a depressed/sad mood or a loss of interest and pleasure, together with five (or more) of the following additional criteria occurring nearly every day i) depressed/sad mood ii) loss of interest and pleasure iii) significant weight loss when not dieting or weight gain or a decrease or increase in appetite iv) insomnia or hypersomnia v) psychomotor agitation or retardation vi) fatigue or loss of energy vii) feelings of worthlessness or excessive or inappropriate guilt viii) diminished ability to think or concentrate or indecisiveness ix) recurrent thoughts of death or suicidal ideation, planning or attempt: 2) the symptoms cause clinically significant distress or impairment in social, occupational or other functioning: 3) the episode is not better accounted for by a psychotic disorder: 4) the episode is not attributable to the physiological effects of a substance or to another medical condition: 5) there has never been a manic or hypomanic episode (Diagnostic and Statistical Manual of Mental Disorders, 5th Edition, American Psychiatric Association, 2013). Other indications contemplated include treating, preventing, or ameliorating one or more symptoms of a disorder including, but not limited to, Rett syndrome, depression, refractory depression, suicidality, obsessive-compulsive disorder, fibromyalgia, post-traumatic stress syndrome, autism spectrum disorder, and depression associated with genetic disorders.

In one embodiment, the major depressive disorder is with anxious distress. In another embodiment, the disorder is with mixed features. In another embodiment, the disorder is with melancholic features. In another embodiment, the disorder is with atypical features. In another embodiment, the disorder is with mood-congruent psychotic features. In another embodiment, the disorder is with mood-incongruent psychotic features. In another embodiment, the disorder is with catatonia. In another embodiment, the disorder is with peripartum onset. In another embodiment, the disorder is with seasonal pattern.

In one embodiment, the major depressive disorder has not responded to adequate doses and treatment duration of antidepressants other than ketamine or esketamine. In some aspects, the non-responder has failed to demonstrate an improvement of up to 25% in MADRS score, or a similar psychometric score, after adequate doses and treatment duration of antidepressants other than ketamine or esketamine. In other aspects, the non-responder has demonstrated an incomplete improvement of between 25-50% in MADRS score, or a similar psychometric score, after adequate doses and treatment duration of antidepressants other than ketamine or esketamine. In other aspects, the non-responder has demonstrated an inadequate improvement of up to 50% in MADRS score, or a similar psychometric score, after adequate doses and treatment duration of antidepressants other than ketamine or esketamine. In some aspects, the adequate doses and treatment duration of antidepressants other than ketamine or esketamine, refers to doses and treatment duration of one, or more, antidepressants other than ketamine or esketamine during the current depressive episode. In other aspects, the adequate course refers to the non-response to doses and treatment duration of one, or more, antidepressants other than ketamine or esketamine during a previous depressive episode. In other aspects, the adequate course refers to the non-response to doses and treatment duration of one, or more, antidepressants other than ketamine or esketamine both during a previous depressive episode and during the current depressive episode. In some aspects, the disorder is treatment-refractory or treatment-resistant depression, i.e., depression that has failed to respond to adequate doses and treatment duration of at least two antidepressants other than ketamine or esketamine.

As used herein, the term "treating major depressive disorder" can refer to a reduction of the symptoms of Major Depressive Disorder, as measured by reduction in the Montgomery-Asberg Depression Rating Scale (MADRS) score. In some aspects, the term "treating major depressive disorder" refers to a change from baseline, as measured the MADRS score. In some aspects, the term "treating major depressive disorder" refers to a remission, as measured by reduction in the MADRS score. In some aspects, the term "treating major depressive disorder" refers to a 50% or greater improvement, as measured the MADRS score.

In other aspects, the term "treating major depressive disorder" refers to change from baseline on Sheehan Disability Scale (SDS).

In other aspects, the term "treating major depressive disorder" refers to change from baseline on self-rated Symptoms of Depression Questionnaire (SDQ).

In other aspects, the term "treating major depressive disorder" refers to change from baseline on the physician-administered Clinical Global Impression Improvement (CGI-I).

In other aspects, the term "treating major depressive disorder" refers to change from baseline on the physician-administered Global Impression Severity (CGI-S).

In other aspects, the term "treating major depressive disorder" refers to change from baseline on Generalized Anxiety Disorder 7 items scale.

In one embodiment, said increases, decreases and reductions of scores and/or presentations of symptoms can be assessed in comparison to the scores and/or presentations of symptoms as identified before treatment is initiated, i.e., baseline. In another embodiment, said increases, decreases and reductions of scores and/or presentations of symptoms can be assessed in comparison to the scores and/or presentations of symptoms as identified in a different treatment group. In one embodiment, the different treatment group is a second medication other than ketamine or esketamine. In another embodiment, the different treatment group is a placebo.

The methods of the disclosure will exhibit an acceptable safety and/or tolerability profile. That is, the benefits achieved using the methods of the disclosure will outweigh any safety and/or tolerability considerations exhibited by using the disclosed methods, as compared to placebo. In other aspects, the benefits achieved using the methods of the disclosure will outweigh any safety and/or tolerability considerations exhibited by using the disclosed methods, as compared to other methods of treating MDD, including treatment-resistant MDD. Other methods of treating MDD, including treatment-resistant MDD include other methods of using ketamine and esketamine. For example, the benefits achieved using the methods of the disclosure will outweigh any adverse events including, for example, untoward changes in hematology, biochemistry, urinalysis, immunological parameters, physical examination findings, blood pressure, and/or heart rate, as compared to placebo. In other aspects, the benefits achieved using the methods of the disclosure will outweigh any adverse events including, for example, changes in hematology, biochemistry, urinalysis, immunological parameters, physical examination findings, blood pressure, and/or heart rate, as compared to other methods of treating MDD, including treatment-resistant MDD.

In other aspects, the benefits achieved using the methods of the disclosure with outweigh any adverse events in 12 lead ECG findings, method discontinuation, Digit Symbol Substitution Test (DSST), reaction time test (Cambridge COGNITION and/or Cogstate battery), self administered Stanford sleepiness scale, a Bladder Pain/Interstitial Cystitis Symptom Score (BPIC-SS), a Modified Observer's Alertness/Sedation Scale (MOAA/S), a Clinician-Administered Dissociative States Scale (CADSS), a Suicidality Scale-Clinician-Rated Columbia Suicide Severity Rating Scale (C-SSRS), 4 items positive symptoms subscale from the Brief Psychiatric Rating Scale (BPRS), and/or 20 item Physician Withdrawal Checklist (PWC-20), as compared to placebo. In other aspects, the benefits achieved using the methods of the disclosure with outweigh any adverse events in 12 lead ECG findings, method discontinuation, Digit Symbol Substitution Test (DSST), reaction time test (Cambridge COGNITION and/or Cogstate battery), self administered Stanford sleepiness scale, a Bladder Pain/Interstitial Cystitis Symptom Score (BPIC-SS), a Modified Observer's Alertness/Sedation Scale (MOAA/S), a Clinician-Administered Dissociative States Scale (CADSS), a Suicidality Scale-Clinician-Rated Columbia Suicide Severity Rating Scale (C-SSRS), 4 items positive symptoms subscale from the Brief Psychiatric Rating Scale (BPRS), and/or 20 item Physician Withdrawal Checklist (PWC-20), as compared to other methods of treating MDD, including treatment-resistant MDD.

As used herein, the term "ketamine" shall refer to the chemical compound dl 2-(2-chlorophenyl)-2(methylamino) cyclohexanone, or a pharmaceutically acceptable salt thereof.

As used herein, the term "esketamine" shall refer to the (S)-enantiomer of ketamine also known as the chemical compound (2S)-2-(2-Chlorophenyl)-2-(methylamino) cyclohexanone, or a pharmaceutically acceptable salt thereof. As used herein, the term "esketamine" shall be understood to be to the exclusion of the compound as found, without an enantiomeric excess, in ketamine, or a pharmaceutically acceptable salt thereof. In one embodiment, the esketamine, or a pharmaceutically acceptable salt thereof, is the hydrochloride salt of esketamine, i.e., esketamine hydrochloride.

As used herein, the term "(R)-ketamine" shall refer to the (R)-enantiomer of ketamine also known as the chemical compound (2R)-2-(2-Chlorophenyl)-2-(methylamino) cyclohexanone, or a pharmaceutically acceptable salt thereof. As used herein, the term "(R)-ketamine" shall be understood to be to the exclusion of the compound as found, without an enantiomeric excess, in ketamine, or a pharmaceutically acceptable salt thereof.

As used herein, the term "(S)-norketamine" shall refer to the (S)-enantiomer of norketamine also known as the chemical compound (2S)-2-(2-Chlorophenyl)-2-(amino) cyclohexanone, or a pharmaceutically acceptable salt thereof. As used herein, the term "(S)-norketamine" shall be understood to be to the exclusion of the compound as found, without an enantiomeric excess, in norketamine, or a pharmaceutically acceptable salt thereof.

As used herein, the term "(2S,6S)—OH-norketamine" shall refer to the (2S,6S)-enantiomer of hydroxynorketamine also known as the chemical compound (2S,6S)-2-Amino-2-(2-chlorophenyl)-6-hydroxycyclohexanone, or a pharmaceutically acceptable salt thereof. As used herein, the term "(2S,6S)—OH-Norketamine" shall be understood to be to the exclusion of the compound as found, without an enantiomeric excess, in hydroxynorketamine, or a pharmaceutically acceptable salt thereof.

The chemical compounds described herein according to the invention are also intended to include such compounds wherein the molecular structures include isotopes of carbon, hydrogen and nitrogen atoms occurring on those structures. Isotopes include those atoms having the same atomic number but different mass numbers. For example, isotopes of hydrogen include deuterium. Isotopes of carbon include $^{13}C$. Isotopes of nitrogen include $^{15}N$.

Accordingly, within the chemical structure of any chemical compound taught in this application as suitable for the formulations disclosed herein:

any hydrogen atom or group of hydrogen atoms, could suitably be replaced by an isotope of hydrogen, i.e., deuterium;

any carbon atom or group of carbon atoms, could suitably be replaced by an isotope of carbon, i.e., $^{13}C$; and any nitrogen atom or group of nitrogen atoms, could suitably be replaced by an isotope of nitrogen, i.e., $^{15}N$.

As used herein, the term "treatment regimen" shall refer to time period during which the human patient, in need thereof, will be treated by more than one, either daily or intermittent, administrations of esketamine. In a preferred embodiment of the invention, the treatment regimen will extend for at least 28 days. In another preferred embodiment, the treatment regimen will extend for at least 30 days. In another preferred embodiment, the treatment regimen will be for 28 days to about 365 days. In another preferred embodiment, the treatment regimen will be for 28 days to about 730 days. Another preferred embodiment, the treatment regimen will extend for at least one month. In another preferred embodiment, the treatment regimen will extend for at least 1 year (365 days). In another preferred embodiment of the invention, the treatment regimen will extend for at least about 730 days, that is, at least about 2 years. In another embodiment, the treatment regimen varies over the course of the 28 to about 730 days (i.e., about two years). A medical professional skilled in the art of psychiatry will be able to determine the administration regimen over the 28 to about 730 days (e.g. about two years).

In one embodiment, the reduction of the symptoms of major depressive disorder are on or after day 28 of the treatment regimen. In another embodiment, the reduction of the symptoms of major depressive disorder are on or after day 30 of the treatment regimen. In another embodiment, the reduction of the symptoms of major depressive disorder are on or after day 365 of the treatment regimen. In another embodiment, the reduction of the symptoms of major depressive disorder are on or after day 730 of the treatment regimen. In one embodiment, the treatment regimen results in a reduction of the symptoms of major depressive disorder after at least 7 days of treatment. In another embodiment, the treatment regimen results in a reduction of the symptoms of major depressive disorder after at least 14 days of treatment. In another embodiment, the treatment regimen results in a reduction of the symptoms of major depressive disorder after at least 21 days of treatment. In another embodiment, the treatment regimen results in a reduction of the symptoms of major depressive disorder after at least 28 days of treatment. In another embodiment, the treatment regimen results in a reduction of the symptoms of major depressive disorder after at least 365 days of treatment. In another embodiment, the treatment regimen results in a reduction of the symptoms of major depressive disorder after at least 730 days of treatment.

In one embodiment, the reduction of the symptoms of major depressive disorder are on or after day 28 of the treatment regimen and are in comparison to the scores and/or presentations of symptoms as identified before treatment is initiated, i.e. baseline. In another embodiment, reduction of the symptoms of major depressive disorder are on or after day 28 of the treatment regimen and are in comparison to the scores and/or presentations of symptoms as identified in a different treatment group. In one embodiment, the different treatment group is a second medication other than ketamine or esketamine. In another embodiment, the different treatment group is a placebo.

It is understood that where a parameter range is provided, all integers within that range, and tenths thereof, are also provided by the invention. For example, "1-30 ng/ml" includes 1.1 ng/ml, 1.2 ng/ml, 1.3 ng/ml, etc. up to 30 ng/ml. In another example, "0.1-2.5 mg/day" includes 0.1 mg/day, 0.2 mg/day, 0.3 mg/day, etc. up to 2.5 mg/day.

The present invention is further directed to a method of treating major depressive disorder in a human patient in need thereof by orally administering to said patient of an oral dosage form comprising about 41 mg and about 80 mg, preferably 41 mg to 80 mg, of esketamine over a treatment regimen of at least 28 days.

In some aspects, oral dosage forms of the disclosure include esketamine, i.e., esketamine as a free base. In other aspects, oral dosage forms of the disclosure include pharmaceutically acceptable salts of esketamine. As used herein, amounts of esketamine present in the oral dosage forms of the disclosure refer to amounts of esketamine free base. For example, in those aspects wherein the oral dosage form comprises esketamine free base, "60 mg of esketamine" refers to 60 mg of the esketamine free base in the oral dosage form. In aspects wherein the oral dosage form comprises a pharmaceutically acceptable salt of esketamine, such as esketamine hydrochloride, "60 mg of esketamine" refers to 60 mg esketamine free base, based on 69.18 mg of esketamine hydrochloride in the oral dosage form.

In one preferred embodiment of the invention, the oral administration to said patient is of an oral dosage form comprising about 45 mg of esketamine, preferably 45 mg of esketamine. In another preferred embodiment of the invention, the oral administration to said patient is of an oral dosage form comprising about 50 mg of esketamine, preferably 50 mg of esketamine. In another preferred embodiment, the oral administration to said patient is of an oral dosage form comprising about 55 mg of esketamine, preferably 55 mg of esketamine. In another preferred embodiment, the oral administration to said patient is of an oral dosage form comprising about 60 mg of esketamine, preferably 60 mg of esketamine. In another preferred embodiment, the oral administration to said patient is of an oral dosage form comprising about 65 mg of esketamine, preferably 65 mg of esketamine. In another preferred embodiment, the oral administration to said patient is of an oral dosage form comprising about 70 mg of esketamine, preferably 70 mg of esketamine. In another preferred embodiment, the oral administration to said patient is of an oral dosage form comprising about 75 mg of esketamine, preferably 75 mg of esketamine. In yet another preferred embodiment, the oral administration to said patient is of an oral dosage form comprising about 80 mg of esketamine, preferably 80 mg of esketamine. In one embodiment of the invention, the oral administration to said patient is of an oral dosage form comprising about 41 to about 45 mg of esketamine, for example, 41 to 45 mg of esketamine. In another embodiment of the invention, the oral administration to said patient is of an oral dosage form comprising about 41 to about 50 mg of esketamine, for example, 41 to 50 mg of esketamine. In another embodiment of the invention, the oral administration to said patient is of an oral dosage form comprising about 41 to about 55 mg of esketamine, for example, 41 to 55 mg of esketamine. In another embodiment of the invention, the oral administration to said patient is of an oral dosage form comprising about 41 to about 60 mg of esketamine, for example, 41 to 60 mg of esketamine. In another embodiment of the invention, the oral administration to said patient is of an oral dosage form comprising about 41 to about 65 mg of esketamine, for example, 41 to 65 mg of esketamine. In another embodiment of the invention, the oral administration to said patient is of an oral dosage form comprising about 41 to about 70 mg of esketamine, for example, 41 to 70 mg of esketamine. In another embodiment of the invention, the oral administration to said patient is of an oral dosage form comprising about 41 to about 75 mg of esketamine, for example, 41 to 75 mg of esketamine. In yet another embodiment of the invention, the oral administration to said patient is of an oral dosage form comprising about 41 to about 80 mg of esketamine, for example, 41 to 80 mg of esketamine. In another embodiment of the invention, the oral administration to said patient is of an oral dosage form comprising about 45 to about 50 mg of esketamine, for example, 45 to 50 mg of esketamine. In another embodiment of the invention, the oral administration to said patient is of an oral dosage form comprising about 45 to about 55 mg of esketamine, for example, 45 to 55 mg of esketamine. In another embodiment of the invention, the oral administration to said patient is of an oral dosage form comprising about 45 to about 60 mg of esketamine, for example, 45 to 60 mg of esketamine. In another embodiment of the invention, the oral administration to said patient is of an oral dosage form comprising about 45 to about 65 mg of esketamine, for example, 45 to 65 mg of esketamine. In another embodiment of the invention, the oral administration to said patient is of an oral dosage form comprising about 45 to about 70 mg of esketamine, for example, 45 to 70 mg of esketamine. In another embodiment of the invention, the oral administration to said patient is of an oral dosage form comprising about 45 to about 75 mg of esketamine, for example, 45 to 75 mg of esketamine. In another embodiment of the invention, the oral administration to said patient is of an oral dosage form comprising about 45 to about 80 mg of esketamine, for example, 45 to 80 mg of esketamine. In another embodiment of the invention, the oral administration to said patient is of an oral dosage form comprising about 50 to about 55 mg of esketamine, for example, 50 to 55 mg of esketamine. In another embodiment of the invention, the oral administration to said patient is of an oral dosage form comprising about 50 to about 60 mg of esketamine, for example, 50 to 60 mg of esketamine. In another embodiment of the invention, the oral administration to said patient is of an oral dosage form comprising about 50 to about 65 mg of esketamine, for example, 50 to 65 mg of esketamine. In another embodiment of the invention, the oral administration to said patient is of an oral dosage form comprising about 50 to about 70 mg of esketamine, for example, 50 to 70 mg of esketamine. In another embodiment of the invention, the oral administration to said patient is of an oral dosage form comprising about 50 to about 75 mg of esketamine, for example, 50 to 75 mg of esketamine. In another embodiment of the invention, the oral administration to said patient is of an oral dosage form comprising about 50 to about 80 mg of esketamine, for example, 50 to 80 mg of esketamine. In another embodiment of the invention, the oral administration to said patient is of an oral dosage form comprising about 55 to about 60 mg of esketamine, for example, 55 to 60 mg of esketamine. In another embodiment of the invention, the oral administration to said patient is of an oral dosage form comprising about 55 to about 65 mg of esketamine, for example, 55 to 65 mg of esketamine. In another embodiment of the invention, the oral administration to said patient is of an oral dosage form comprising about 55 to about 70 mg of esketamine, for example, 55 to 70 mg of esketamine. In another embodiment of the invention, the oral administration to said patient is of an oral dosage form comprising about 55 to about 75 mg of esketamine, for example, 55 to 75 mg of esketamine. In another embodiment of the invention, the oral administration to said patient is of an oral dosage form comprising about 55 to about 80 mg of esketamine, for example, 55 to 80 mg of esketamine. In another embodiment of the invention, the oral administration to said patient is of an oral dosage form comprising about 60 to about 65 mg of esketamine, for example, 60 to 65 mg of esketamine. In another embodiment of the invention, the oral administration to said patient is of an oral dosage form comprising about 60 to about 70 mg of esketamine, for example, 60 to 70 mg of esketamine. In another embodiment of the invention, the oral administration to said patient is of an oral dosage form comprising about 60 to about 75 mg of esketamine, for example, 60 to 75 mg of esketamine. In another embodiment of the invention, the oral administration to said patient is of an oral dosage form comprising about 60 to about 80 mg of esketamine, for example, 60 to 80 mg of esketamine. In another embodiment of the invention, the oral administration to said patient is of an oral dosage form comprising about 65 to about 70 mg of esketamine, for example, 65 to 70 mg of esketamine. In another embodiment of the invention, the oral administration to said patient is of an oral dosage form comprising about 65 to about 75 mg of esketamine, for example, 65 to 75 mg of esketamine. In another embodiment of the invention, the oral administration to said patient is of an oral dosage form comprising about 65 to about 80 mg of esketamine, for example, 65 to 80 mg of esketamine. In another embodiment of the invention, the oral administration to said patient is of an oral dosage form comprising about 70 to about 75 mg of esketamine, for example, 70 to 75 mg of esketamine. In another embodiment of the invention, the oral administration to said patient is of an oral dosage form comprising about 70 to about 80 mg of esketamine, for example, 70 to 80 mg of esketamine. In another embodiment of the invention, the oral administration to said patient is of an oral dosage form comprising about 75 to about 80 mg of esketamine, for example, 75 to 80 mg of esketamine.

Without wanting to be bound to any particular theory, it is believed that a therapeutic effect of repeated oral dosing of esketamine in the treatment of major depressive disorder can be achieved by either administering higher doses of the drug at longer intervals or administering lower doses of the drug at shorter intervals. As described herein, the present invention allows for equivalent exposure over time of the drug and its metabolites and lower peak concentrations, reduces the overall risk of genotoxic events and improves the clinical safety profile.

The present invention is further directed to a method of treating major depressive disorder in a human patient in need thereof by the oral administration to said patient of an oral dosage form comprising about 41 mg and about 80 mg of esketamine, preferably 41 mg to 80 mg of esketamine, wherein the esketamine $C_{max}$ of said administration is 30 ng/ml or less.

As used herein, the term "$C_{max}$" shall refer to the mean (average) observed maximum plasma concentration assayed after any single administration. In some embodiments the method disclosed herein further comprises measuring plasma levels in the patient.

In one embodiment of the invention, the esketamine $C_{max}$ of said administration is 30 ng/ml or less, 29 ng/ml or less, 28 ng/ml or less, 27 ng/ml or less, 26 ng/ml or less, 25 ng/ml or less, 24 ng/ml or less, 23 ng/ml or less, 22 ng/ml or less, 21 ng/ml or less, 20 ng/ml or less, 19 ng/ml or less, 18 ng/ml or less, 17 ng/ml or less, 16 ng/ml or less, 15 ng/ml or less, 14 ng/ml or less, 13 ng/ml or less, 12 ng/ml or less, 11 ng/ml or less, 10 ng/ml or less, 9 ng/ml or less, 8 ng/ml or less, 7 ng/ml or less, 6 ng/ml or less, 5 ng/ml or less, 4 ng/ml or less, 3 ng/ml or less, 2 ng/ml or less, or 1 ng/ml or less. In one preferred embodiment of the invention, the esketamine $C_{max}$ of said administration is 30 ng/ml or less. In another preferred embodiment of the invention, the esketamine $C_{max}$ of said administration is 15 ng/ml or less. In one preferred embodiment of the invention, the esketamine $C_{max}$ of said administration is between 15 ng/mL and 30 ng/mL. In one preferred embodiment of the invention, the esketamine $C_{max}$ of said administration is between 10 ng/mL and 15 ng/mL. In one preferred embodiment of the invention, the esketamine $C_{max}$ of said administration is between 5 ng/mL and 15 ng/mL. In one preferred embodiment of the invention, the esketamine $C_{max}$ of said administration is between 11 ng/mL and 13 ng/mL.

The present invention is further directed to a method of treating major depressive disorder in a human patient in need thereof by the oral administration to said patient of an oral dosage form comprising about 41 mg and about 80 mg of esketamine, for example, 41 mg to 80 mg of esketamine, wherein the esketamine $AUC_{0-t}$ of said administration is 60 ng*h/ml or less.

As used herein, the term "AUC" shall refer to the area under the plasma concentration/time curve after any single administration. The term "$AUC_{0-t}$" shall refer to the area under the plasma concentration/time curve from time 0 to the last quantifiable concentration after any single administration and the term "$AUC_{0-inf}$" shall refer to the area under the plasma concentration/time curve from time 0 until the extrapolated concentration at infinity after any single administration. The term "$AUC_{tau}$" shall refer to the area under the plasma concentration/time curve over the steady state dosing interval.

In one embodiment of the invention, the esketamine $AUC_{0-t}$ of said administration is 60 ng*h/ml, 59 ng*h/ml, 58 ng*h/ml, 57 ng*h/ml, 56 ng*h/ml, 55 ng*h/ml, 54 ng*h/ml, 53 ng*h/ml, 52 ng*h/ml, 51 ng*h/ml, 50 ng*h/ml, 49 ng*h/ml, 48 ng*h/ml, 47 ng*h/ml, 46 ng*h/ml, 45 ng*h/ml, 44 ng*h/ml, 43 ng*h/ml, 42 ng*h/ml, 41 ng*h/ml, 40 ng*h/ml, 39 ng*h/ml, 38 ng*h/ml, 37 ng*h/ml, 36 ng*h/ml, 35 ng*h/ml, 34 ng*h/ml, 33 ng*h/ml, 32 ng*h/ml, 31 ng*h/ml, 30 ng*h/ml, 29 ng*h/ml, 28 ng*h/ml, 27 ng*h/ml, 26 ng*h/ml, 25 ng*h/ml, 24 ng*h/ml, 23 ng*h/ml, 22 ng*h/ml, 21 ng*h/ml, 20 ng*h/ml, 19 ng*h/ml, 18 ng*h/ml, 17 ng*h/ml, 16 ng*h/ml, 15 ng*h/ml, 14 ng*h/ml, 13 ng*h/ml, 12 ng*h/ml, 11 ng*h/ml, 10 ng*h/ml, 9 ng*h/ml, 8 ng*h/ml, 7 ng*h/ml, 6 ng*h/ml, 5 ng*h/ml, 4 ng*h/ml, 3 ng*h/ml, 2 ng*h/ml, or 1 ng*h/ml. In one preferred embodiment of the invention, the esketamine $AUC_{0-t}$ of said administration is 60 ng*h/ml or less. In another preferred embodiment of the invention, the esketamine $AUC_{0-t}$ of said administration is 30 ng*h/ml or less. In one preferred embodiment of the invention, the esketamine $AUC_{0-t}$ of said administration is between 30 ng*h/ml and 60 ng*h/ml. In one preferred embodiment of the invention, the esketamine $AUC_{0-t}$ of said administration is between 15 ng*h/ml and 30 ng*h/ml.

The present invention is further directed to a method of treating major depressive disorder in a human patient in need thereof by the oral administration to said patient of a dosage form, wherein said dosage form provides for an (S)-norketamine $C_{max}$ of 150 ng/ml or less.

In one embodiment of the invention, the (S)-norketamine $C_{max}$ of said administration is 150 ng/ml or less, 145 ng/ml or less, 140 ng/ml or less, 139 ng/ml or less, 138 ng/ml or less, 137 ng/ml or less, 136 ng/ml or less, 135 ng/ml or less, 134 ng/ml or less, 133 ng/ml or less, 132 ng/ml or less, 131 ng/ml or less, 130 ng/ml or less, 129 ng/ml or less, 128 ng/ml or less, 127 ng/ml or less, 126 ng/ml or less, 125 ng/ml or less, 120 ng/ml or less, 115 ng/ml or less, 110 ng/ml or less, 105 ng/ml or less, 100 ng/ml or less, 95 ng/ml or less, 90 ng/ml or less, 85 ng/ml or less, 80 ng/ml or less, 75 ng/ml or less, 74 ng/ml or less, 73 ng/ml or less, 72 ng/ml or less, 71 ng/ml or less, 70 ng/ml or less, 69 ng/ml or less, 68 ng/ml or less, 67 ng/ml or less, 66 ng/ml or less, 65 ng/ml or less, 64 ng/ml or less, 63 ng/ml or less, 62 ng/ml or less, 61 ng/ml or less, 60 ng/ml or less, 55 ng/ml or less, 50 ng/ml or less, 45 ng/ml or less, 40 ng/ml or less, 35 ng/ml or less, 34 ng/ml or less, 33 ng/ml or less, 32 ng/ml or less, 31 ng/ml or less, 30 ng/ml or less, 25 ng/ml or less, 20 ng/ml or less, 19 ng/ml or less, 18 ng/ml or less, 17 ng/ml or less, 16 ng/ml or less or 15 ng/ml or less. In one preferred embodiment of the invention, the (S)-norketamine $C_{max}$ of said administration is 150 ng/ml or less. In another preferred embodiment of the invention, the (S)-norketamine $C_{max}$ of said administration is 75 ng/ml or less. In another preferred embodiment of the invention, the (S)-norketamine $C_{max}$ of said administration is 35 ng/ml or less. In another preferred embodiment of the invention, the (S)-norketamine $C_{max}$ of said administration is 20 ng/ml or less. In one preferred embodiment of the invention, the (S)-norketamine $C_{max}$ of said administration is between 15 ng/mL and 150 ng/mL. In another preferred embodiment of the invention, the (S)-norketamine $C_{max}$ of said administration is between 15 ng/mL and 20 ng/mL. In another preferred embodiment of the invention, the (S)-norketamine $C_{max}$ of said administration is between 30 ng/mL and 35 ng/mL. In another preferred embodiment of the invention, the (S)-norketamine $C_{max}$ of said administration is between 60 ng/mL and 75 ng/mL. In another preferred embodiment of the invention, the (S)-norketamine $C_{max}$ of said administration is between 125 ng/mL and 140 ng/mL. In another preferred embodiment of the invention, the (S)-norketamine $C_{max}$ of said administration is between 60 ng/mL and 140 ng/mL.

The present invention is further directed to a method of treating major depressive disorder in a human patient in need thereof by the oral administration to said patient of a dosage form, wherein said dosage form provides for an (S)-norketamine $AUC_{0-t}$ of 850 ng*h/ml or less.

In one embodiment of the invention, the (S)-norketamine $AUC_{0-t}$ of said administration is 850 ng*h/ml or less, 845 ng*h/ml or less, 840 ng*h/ml or less, 839 ng*h/ml or less, 838 ng*h/ml or less, 837 ng*h/ml or less, 836 ng*h/ml or less, 835 ng*h/ml or less, 834 ng*h/ml or less, 832 ng*h/ml or less, 831 ng*h/ml or less, 830 ng*h/ml or less, 829 ng*h/ml or less, 828 ng*h/ml or less, 827 ng*h/ml or less, 826 ng*h/ml or less, 825 ng*h/ml or less, 824 ng*h/ml or less, 823 ng*h/ml or less, 822 ng*h/ml or less, 821 ng*h/ml or less, 820 ng*h/ml or less, 815 ng*h/ml or less, 810 ng*h/ml or less, 805 ng*h/ml or less, 800 ng*h/ml or less, 795 ng*h/ml or less, 790 ng*h/ml or less, 785 ng*h/ml or less, 780 ng*h/ml or less, 775 ng*h/ml or less, 770 ng*h/ml or less, 765 ng*h/ml or less, 760 ng*h/ml or less, 755 ng*h/ml or less, 750 ng*h/ml or less, 745 ng*h/ml or less, 740 ng*h/ml or less, 735 ng*h/ml or less, 730 ng*h/ml or less, 725 ng*h/ml or less, 720 ng*h/ml or less, 710 ng*h/ml or less, 700 ng*h/ml or less, 690 ng*h/ml or less, 680 ng*h/ml or less, 670 ng*h/ml or less, 660 ng*h/ml or less, 650 ng*h/ml or less, 640 ng*h/ml or less, 630 ng*h/ml or less, 620 ng*h/ml or less, 610 ng*h/ml or less, 600 ng*h/ml or less, 590 ng*h/ml or less, 580 ng*h/ml or less, 570 ng*h/ml or less, 560 ng*h/ml or less, 550 ng*h/ml or less, 540 ng*h/ml or less, 530 ng*h/ml or less, 520 ng*h/ml or less, 510 ng*h/ml or less, 500 ng*h/ml or less, 490 ng*h/ml or less, 480 ng*h/ml or less, 470 ng*h/ml or less, 460 ng*h/ml or less, 450 ng*h/ml or less, 440 ng*h/ml or less, 430 ng*h/ml or less, 425 ng*h/ml or less, 420 ng*h/ml or less, 419 ng*h/ml or less, 418 ng*h/ml or less, 417 ng*h/ml or less, 416 ng*h/ml or less, 415 ng*h/ml or less, 414 ng*h/ml or less, 413 ng*h/ml or less, 412 ng*h/ml or less, 411 ng*h/ml or less, 410 ng*h/ml or less, 405 ng*h/ml or less, 400 ng*h/ml or less, 390 ng*h/ml or less, 380 ng*h/ml or less, 380 ng*h/ml or less, 370 ng*h/ml or less, 360 ng*h/ml or less, 350 ng*h/ml or less, 340 ng*h/ml or less, 330 ng*h/ml or less, 320 ng*h/ml or less, 310 ng*h/ml or less, 300 ng*h/ml or less, 290 ng*h/ml or less, 280 ng*h/ml or less, 270 ng*h/ml or less, 260 ng*h/ml or less, 250 ng*h/ml or less, 240 ng*h/ml or less, 230 ng*h/ml or less, 220 ng*h/ml or less, 215 ng*h/ml or less, 210 ng*h/ml or less, 209 ng*h/ml or less, 208 ng*h/ml or less, 207 ng*h/ml or less, 206 ng*h/ml or less, 205 ng*h/ml or less, 200 ng*h/ml or less, 190 ng*h/ml or less, 180 ng*h/ml or less, 170 ng*h/ml or less, 160 ng*h/ml or less, 150 ng*h/ml or less, 140 ng*h/ml or less, 130 ng*h/ml or less, 120 ng*h/ml or less, 110 ng*h/ml or less, 105 ng*h/ml or less, 104 ng*h/ml or less, 103 ng*h/ml or less or 102 ng*h/ml or less. In one preferred embodiment of the invention, the (S)-norketamine $AUC_{0-t}$ of said administration is 850 ng*h/ml or less. In another preferred embodiment of the invention, the (S)-norketamine $AUC_{0-t}$ of said administration is 420 ng*h/ml or less. In another preferred embodiment of the invention, the (S)-norketamine $AUC_{0-t}$ of said administration is 210 ng*h/ml or less. In another preferred embodiment of the invention, the (S)-norketamine $AUC_{0-t}$ of said administration is 105 ng*h/ml or less. In one preferred embodiment of the invention, the (S)-norketamine $AUC_{0-t}$ of said administration is between 105 ng*h/ml and 850 ng*h/ml. In another preferred embodiment of the invention, the (S)-norketamine $AUC_{0-t}$ of said administration is between 105 ng*h/ml and 850 ng*h/ml. In another preferred embodiment of the invention, the (S)-norketamine $AUC_{0-t}$ of said administration is between 102 ng*h/ml and 105 ng*h/ml. In another preferred embodiment of the invention, the (S)-norketamine $AUC_{0-t}$ of said administration is between 205 ng*h/ml and 210 ng*h/ml. In another preferred embodiment of the invention, the (S)-norketamine $AUC_{0-t}$ of said administration is between 410 ng*h/ml and 420 ng*h/ml. In another preferred embodiment of the invention, the (S)-norketamine $AUC_{0-t}$ of said administration is between 820 ng*h/ml and 840 ng*h/ml.

The present invention is further directed to a method of treating major depressive disorder in a human patient in need thereof by the oral administration to said patient of a dosage form, wherein said dosage form provides for an (2S,6S)—OH-norketamine $C_{max}$ of 75 ng/ml or less.

In one embodiment of the invention, the (2S,6S)—OH-norketamine $C_{max}$ of said administration is 75 ng/ml or less, 74 ng/ml or less, 73 ng/ml or less, 72 ng/ml or less, 71 ng/ml or less, 70 ng/ml or less, 69 ng/ml or less, 68 ng/ml or less, 67 ng/ml or less, 66 ng/ml or less, 65 ng/ml or less, 64 ng/ml or less, 63 ng/ml or less, 62 ng/ml or less, 61 ng/ml or less, 60 ng/ml or less, 55 ng/ml or less, 50 ng/ml or less, 45 ng/ml or less, 40 ng/ml or less, 35 ng/ml or less, 34 ng/ml or less, 33 ng/ml or less, 32 ng/ml or less, 31 ng/ml or less, 30 ng/ml or less, 25 ng/ml or less, 20 ng/ml or less, 19 ng/ml or less, 18 ng/ml or less, 17 ng/ml or less, 16 ng/ml or less or 15 ng/ml or less. In one preferred embodiment of the invention, the (2S,6S)—OH-norketamine $C_{max}$ of said administration is 75 ng/ml or less. In another preferred embodiment of the invention, the (2S,6S)—OH-norketamine $C_{max}$ of said administration is 35 ng/ml or less. In another preferred embodiment of the invention, the (2S,6S)—OH-norketamine $C_{max}$ of said administration is 20 ng/ml or less. In one preferred embodiment of the invention, the (2S,6S)—OH-norketamine $C_{max}$ of said administration is between 15 ng/mL and 75 ng/mL. In another preferred embodiment of the invention, the (2S,6S)—OH-norketamine $C_{max}$ of said administration is between 15 ng/mL and 20 ng/mL. In another preferred embodiment of the invention, the (2S,6S)—OH-norketamine $C_{max}$ of said administration is between 30 ng/mL and 35 ng/mL. In another preferred embodiment of the invention, the (2S,6S)—OH-norketamine $C_{max}$ of said administration is between 60 ng/mL and 75 ng/mL.

The present invention is further directed to a method of treating major depressive disorder in a human patient in need thereof by the oral administration to said patient of a dosage form, wherein said dosage form provides for an (2S,6S)—OH-norketamine $AUC_{0-t}$ of 850 ng*h/ml or less.

In one embodiment of the invention, the (2S,6S)—OH-norketamine $AUC_{0-t}$ of said administration is 850 ng*h/ml or less, 845 ng*h/ml or less, 840 ng*h/ml or less, 839 ng*h/ml or less, 838 ng*h/ml or less, 837 ng*h/ml or less, 836 ng*h/ml or less, 835 ng*h/ml or less, 834 ng*h/ml or less, 832 ng*h/ml or less, 831 ng*h/ml or less, 830 ng*h/ml or less, 829 ng*h/ml or less, 828 ng*h/ml or less, 827 ng*h/ml or less, 826 ng*h/ml or less, 825 ng*h/ml or less, 824 ng*h/ml or less, 823 ng*h/ml or less, 822 ng*h/ml or less, 821 ng*h/ml or less, 820 ng*h/ml or less, 815 ng*h/ml or less, 810 ng*h/ml or less, 805 ng*h/ml or less, 800 ng*h/ml or less, 795 ng*h/ml or less, 790 ng*h/ml or less, 785 ng*h/ml or less, 780 ng*h/ml or less, 775 ng*h/ml or less, 770 ng*h/ml or less, 765 ng*h/ml or less, 760 ng*h/ml or less, 755 ng*h/ml or less, 750 ng*h/ml or less, 745 ng*h/ml or less, 740 ng*h/ml or less, 735 ng*h/ml or less, 730 ng*h/ml or less, 725 ng*h/ml or less, 720 ng*h/ml or less, 710 ng*h/ml or less, 700 ng*h/ml or less, 690 ng*h/ml or less, 680 ng*h/ml or less, 670 ng*h/ml or less, 660 ng*h/ml or less, 650 ng*h/ml or less, 640 ng*h/ml or less, 630 ng*h/ml or less, 620 ng*h/ml or less, 610 ng*h/ml or less, 600 ng*h/ml or less, 590 ng*h/ml or less, 580 ng*h/ml or less, 570 ng*h/ml or less, 560 ng*h/ml or less, 550 ng*h/ml or less, 540 ng*h/ml or less, 530 ng*h/ml or less, 520 ng*h/ml or less, 510 ng*h/ml or less, 500 ng*h/ml or less, 490 ng*h/ml or less, 480 ng*h/ml or less, 470 ng*h/ml or less, 460 ng*h/ml or less, 450 ng*h/ml or less, 440 ng*h/ml or less, 430 ng*h/ml or less, 425 ng*h/ml or less, 420 ng*h/ml or less, 419 ng*h/ml or less, 418 ng*h/ml or less, 417 ng*h/ml or less, 416 ng*h/ml or less, 415 ng*h/ml or less, 414 ng*h/ml or less, 413 ng*h/ml or less, 412 ng*h/ml or less, 411 ng*h/ml or less, 410 ng*h/ml or less, 405 ng*h/ml or less, 400 ng*h/ml or less, 390 ng*h/ml or less, 380 ng*h/ml or less, 380 ng*h/ml or less, 370 ng*h/ml or less, 360 ng*h/ml or less, 350 ng*h/ml or less, 340 ng*h/ml or less, 330 ng*h/ml or less, 320 ng*h/ml or less, 310 ng*h/ml or less, 300 ng*h/ml or less, 290 ng*h/ml or less, 280 ng*h/ml or less, 270 ng*h/ml or less, 260 ng*h/ml or less, 250 ng*h/ml or less, 240 ng*h/ml or less, 230 ng*h/ml or less, 220 ng*h/ml or less, 215 ng*h/ml or less, 210 ng*h/ml or less, 209 ng*h/ml or less, 208 ng*h/ml or less, 207 ng*h/ml or less, 206 ng*h/ml or less, 205 ng*h/ml or less, 200 ng*h/ml or less, 190 ng*h/ml or less, 180 ng*h/ml or less, 170 ng*h/ml or less, 160 ng*h/ml or less, 150 ng*h/ml or less, 140 ng*h/ml or less, 130 ng*h/ml or less, 120 ng*h/ml or less, 110 ng*h/ml or less, 105 ng*h/ml or less, 104 ng*h/ml or less, 103 ng*h/ml or less or 102 ng*h/ml or less. In one preferred embodiment of the invention, the (2S,6S)—OH-norketamine $AUC_{0-t}$ of said administration is 850 ng*h/ml or less. In another preferred embodiment of the invention, the (2S,6S)—OH-norketamine $AUC_{0-t}$ of said administration is 420 ng*h/ml or less. In another preferred embodiment of the invention, the (2S,6S)—OH-norketamine $AUC_{0-t}$ of said administration is 210 ng*h/ml or less. In another preferred embodiment of the invention, the (2S,6S)—OH-norketamine $AUC_{0-t}$ of said administration is 105 ng*h/ml or less. In one preferred embodiment of the invention, the (2S,6S)—OH-norketamine $AUC_{0-t}$ of said administration is between 105 ng*h/ml and 850 ng*h/ml. In another preferred embodiment of the invention, the (2S,6S)—OH-norketamine $AUC_{0-t}$ of said administration is between 105 ng*h/ml and 850 ng*h/ml. In another preferred embodiment of the invention, the (2S,6S)—OH-norketamine $AUC_{0-t}$ of said administration is between 102 ng*h/ml and 105 ng*h/ml. In another preferred embodiment of the invention, the (2S,6S)—OH-norketamine $AUC_{0-t}$ of said administration is between 205 ng*h/ml and 210 ng*h/ml. In another preferred embodiment of the invention, the (2S,6S)—OH-norketamine $AUC_{0-t}$ of said administration is between 410 ng*h/ml and 420 ng*h/ml. In another preferred embodiment of the invention, the (2S,6S)—OH-norketamine $AUC_{0-t}$ of said administration is between 820 ng*h/ml and 840 ng*h/ml.

The present invention is further directed to a method of treating major depressive disorder, in a human patient in need thereof by the oral administration to said patient of an oral dosage form comprising between about 41 mg and about 80 mg of esketamine, for example, 41 mg to 80 mg, of esketamine, wherein the administration is daily.

In one embodiment of the invention, the daily administration of esketamine is provided in a single daily dose. In another embodiment of the invention, the daily administration of esketamine is provided in two doses, in three doses, or in four doses, each dose being spread about equally over the 24 hour period.

The present invention is further directed to a method of treating major depressive disorder in a human patient in need thereof by the oral administration to said patient of an oral dosage form comprising about 41 mg to about 80 mg of esketamine, preferably 41 mg to 80 mg of esketamine, wherein the administration is intermittent over the treatment regimen.

In a preferred embodiment of the invention, the intermittent administration is once every second day to about once a month or once every 4 weeks. In one embodiment of the invention, the intermittent administration is once every second day, once every third day, twice a week, once every fourth day, once every fifth day, once every sixth day, once a week, once every eighth day, once every ninth day, once every tenth day, once every eleventh day, once every twelfth day, once every thirteenth day, once every two weeks, once every three weeks or once a month. In one preferred embodiment of the invention, the intermittent administration is twice a week. In another preferred embodiment of the invention, the intermittent administration is once a week. In yet another preferred embodiment of the invention, the intermittent administration is once a month. In yet another preferred embodiment of the invention, the intermittent administration is once every 4 weeks.

In one embodiment of the invention, frequency of the intermittent administration can vary over the time period of the treatment regimen. In a preferred embodiment of the invention, the frequency of the intermittent administration is gradually reduced over the time period of the treatment regimen. In a more preferred embodiment of the invention, the frequency of the intermittent administration is reduced from twice a week to once a week. In another preferred embodiment of the invention, the frequency of the intermittent administration is reduced from once a week to once every two weeks. In an even more preferred embodiment of the invention, the frequency of the intermittent administration is reduced from twice a week to once a week to once every two weeks. In another preferred embodiment of the invention, the frequency of the intermittent administration is maintained consistently over the time period of the treatment regimen.

The present invention is further directed to a method of treating major depressive disorder in a human patient in need thereof by the oral administration to said patient of an oral dosage form comprising between about 41 mg and about 80 mg of esketamine, preferably 41 mg to 80 mg of esketamine, over a treatment regimen of at least 28 days wherein the administration is self-administered. As used herein "self-administered" refers to administration wherein the patient is responsible for taking the medication and is not assisted during the oral administration of the oral dosage form by a healthcare professional. In some aspects, one or more of the administrations may be assisted by a healthcare professional and one or more of the administration may be self-administered over the treatment regimen. In one embodiment, said self-administration is in the patient's own home. In a preferred embodiment, said self-administration is at night. In a more preferred embodiment, said self-administration is before the patient goes to sleep.

In another embodiment, the patient has no restrictions on driving in the 24 hours immediately following the oral administration of the oral dosage form comprising about between about 41 mg to about 80 mg of esketamine, preferably 41 mg to 80 mg of esketamine. That is, the oral administration of the oral dosage form does not result in a mental or motor impairment that negatively affects the patient's ability to operative a motor vehicle. In the 24 hours immediately following the administration.

In yet another embodiment, the patient is restricted from driving for no more than 10 hours after the oral administration of the oral dosage form comprising about 41 mg to about 80 mg of esketamine, preferably 41 mg to 80 mg of esketamine. In a preferred embodiment, the patient is restricted from driving for no more than 8 hours after the administration. In another preferred embodiment, the patient is restricted from driving for no more than 6 hours after the administration. In a more preferred embodiment, the patient is restricted from driving for no more than 2 hours after the administration. In a most preferred embodiment, the patient is restricted from driving for no more than an hour after the oral administration of the oral dosage form comprising about 41 mg to about 80 mg of esketamine, preferably 41 mg to 80 mg of esketamine.

In one embodiment of the invention, the oral dosage form is a liquid preparation such as a suspension, elixir, or solution. In another embodiment of the invention, the oral dosage forms are solid preparations, for example, powders, capsules, caplets, gelcaps, and tablets. In a preferred embodiment, the oral dosage form is a tablet, gelcap, or capsule. In a more preferred embodiment, the oral dosage form is a tablet.

To prepare the preparations, i.e., the oral dosage forms, of this invention, esketamine, and optionally, at least one second medication other than (R)-ketamine, are admixed with pharmaceutical carriers according to conventional pharmaceutical compounding techniques, which carriers may take a wide variety of forms depending of the form of preparation desired for administration. In preparing the oral preparations, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like. For solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed.

The present invention is further directed to a method of treating major depressive disorder in a human patient in need thereof by the administration to said patient of an oral dosage form comprising about 41 mg to about 80 mg of esketamine, preferably 41 mg to 80 mg of esketamine, wherein the oral dosage form is an abuse deterrent formulation. In a more preferred embodiment, the abuse deterrent formulation is a tablet. Abuse deterrent tablet formulations can be prepared by methods known in the art including as found in U.S. Pat. No. 7,955,619, WO2014006004, WO2008033523, WO2008023261, WO2016094358, WO2020225773 and US2004052731 each of which is hereby incorporated by reference.

The present invention is further directed to methods of treating major depressive disorder in a human patient in need thereof by the oral administration to said patient of an oral dosage form comprising about 41 mg to about 80 mg of esketamine, preferably 41 mg to 80 mg of esketamine, further comprising the administration of a second medication other than (R)-ketamine.

In a preferred embodiment, the second medication is an antidepressant, an antimanic agent or an anxiolytic drug. In one embodiment of the invention, the antidepressant is selected from the group consisting of mono-amine oxidase inhibitors (MAOI), tricyclic antidepressants (TCA), serotonin specific reuptake inhibitors (SSRI), serotonin noradrenergic reuptake inhibitors (SNRI), noradrenaline reuptake inhibitor (NRI), "natural products" (such as Kava-Kava, St. John's Wort), dietary supplement (such as s-adenosylmethionine) and others. More specifically, antidepressants include, but are not limited to, imipramine, amitriptyline, desipramine, nortriptyline, doxepin, protriptyline, trimipramine, maprotiline, amoxapine, trazodone, bupropion, chlomipramine, fluoxetine, citalopram, escitalopram, sertraline, paroxetine, tianeptine, agomelatine, nefazadone, venlafaxine, desvenlafaxine, vilazodone, vortioxetine, duloxetine, reboxetine, mirtazapine, mianserin, phenelzine, tranylcypromine, and/or moclobemide.

In another preferred embodiment, the second medication is an antimanic agent. In one embodiment of the invention, the antimanic agent is selected from the group consisting of carbamazepine, gabapentin, Lithium or a pharmaceutically acceptable salt thereof, valproic acid and antipsychotic medications such as lurasidone, cariprazine, olanzapine, risperidone, quetiapine, paliperidone, aripiprazole and brexpiprazole.

In another preferred embodiment, the second medication is an anxiolytic drug. In one embodiment of the invention, the anxiolytic drug is selected from the group consisting of Alprazolam, Bromazepam, Chlordiazepoxide, Clonazepam, Clorazepate, Diazepam, Flurazepam, Lorazepam, Oxazepam, Temazepam, Triazolam, Buspirone, Gepirone, Ispapirone, Hydroxyzine, Amobarbital, Pentobarbital, Phenobarbital, Thiopental and Propanolol.

The present invention is further directed to a method of treating major depressive disorder in a human patient in need thereof, by the oral administration to said patient of an oral dosage form comprising about 41 mg to about 80 mg of esketamine, preferably 41 mg to 80 mg of esketamine and an antidepressant selected from the group consisting of fluoxetine, sertraline, paroxetine, citalopram, escitalopram, venlafaxine, desvenlafaxine, duloxetine, and fluvoxamine and wherein the administration is daily over a treatment regimen of at least 28 days.

This invention will be better understood by reference to the Examples, which follow, but those skilled in the art will readily appreciate that the specific experiments detailed are only illustrative of the invention as described more fully in the claims which follow thereafter.

EXAMPLES

Example 1: In Vitro Chromosomal Aberration Assay

Example 1a: Esketamine

The clastogenic potential of esketamine was evaluated in the in vitro mammalian chromosome aberration test using human peripheral blood lymphocytes (HPBL) in both the absence and presence of an induced metabolic activation system (the 9000 g supernatant [S9] microsomal fraction of liver homogenate from rats exposed to Aroclor-1254). Clastogenicity was evaluated by microscopic examination of HPBL in metaphase to determine the mitotic index (MI) and percentage of metaphase cells with numerical and/or structural chromosome aberrations.

The study was conducted in 2 phases, with a preliminary toxicity test used to determine the appropriate concentrations for the definitive chromosomal aberration assay. Water was used as a negative (vehicle) control. Toxicity (defined as ≥45% reduction in MI relative to the vehicle control) was evaluated at 9 concentrations, ranging from 0.0238 to 238 µg/ml, after exposure of HPBL to esketamine for 20 hours in the absence of S9 activation, or for 4 hours, either in the presence or absence of S9 activation, followed by a 16-hour recovery period. Toxicity was not observed at any dose in any of the three treatment conditions. Based upon these results, the doses chosen for the chromosomal aberration assay ranged from 30 to 238 µg/ml for all three treatment conditions. All concentrations were between 98% to 101% of the nominal concentrations.

The definitive chromosome aberration assay evaluated HPBL cells after exposure to esketamine for 20 hours in the absence of S9 activation, or for 4 hours, either in the presence of absence of S9 activation, followed by a 16-hour recovery. Positive controls for chromosomal aberrations in non-activated and S9-activated evaluations, respectively, consisted of mitomycin C (MMC, 0.6 and 0.3 µg/mL for the 4- and 20-hour exposures, respectively) and cyclophosphamide (CP, 2.5, 5, and 7.5 µg/mL). Water was associated with mean MI values from 13.4% to 16.5% and numerical or structural chromosomal aberrations in 0% to 0.7% of the cells. In non-activated systems, MMC was associated with a mean MI value of 9% with structural chromosomal aberrations in 13.3% of the cells. In the S9-activated system, CP was associated with a mean MI value of 6.2% and with structural aberrations in 10.7% of the cells. The results for negative controls were within the range of historical controls and the results for positive controls were statistically significant ($p \leq 0.01$, Fisher's exact test). Thus the requirements for a valid test were fulfilled. In the chromosomal aberration assay, cytotoxicity (≥45% reduction in mitotic index relative to the vehicle control) was not observed at any esketamine dose in the non-activated 4- and 20-hour treatment conditions. Cytotoxicity was observed at doses ≥200 µg/mL in the S9-activated 4-hour exposure group. Initially, the doses selected for evaluation of chromosomal aberrations were 60, 120, and 238 µg/mL for the non-activated 4- and 20-hour treatment conditions; and 30, 60, and 200 µg/mL for the S9-activated 4-hour treatment condition.

In the non-activated 4 and 20-hour exposure groups, no significant or dose-dependent increases in structural or numerical (polyploid or endoreduplicated cells) aberrations were observed at any dose ($p > 0.05$; Fisher's Exact and Cochran-Armitage tests).

In the S9-activated 4-hour exposure group, a statistically significant increase (5.0%) in structural aberrations was observed at 200 µg/mL ($p \leq 0.01$; Fisher's Exact test). In order to confirm that the statistical significance observed at the high dose was not due to cytotoxicity, a lower dose (120 µg/mL) was included in the evaluation. A statistically significant increase (4.3%) in structural aberrations was observed at 120 µg/mL ($p \leq 0.01$; Fisher's Exact test). The Cochran-Armitage test was positive for a dose response ($p \leq 0.01$). No significant or dose-dependent increases in numerical (polyploid or endoreduplicated cells) aberrations were observed at any dose ($p > 0.05$; Fisher's Exact and Cochran-Armitage tests).

The results of the study indicate that esketamine was positive for the induction of structural chromosomal aberrations and negative for the induction of numerical chromosomal aberrations in the presence of the exogenous metabolic activation system. Esketamine was negative for the induction of structural and numerical chromosomal aberrations in the absence of the exogenous metabolic activation system.

Example 1b: (S)-norketamine

The clastogenic potential of (S)-norketamine was evaluated in the in vitro mammalian chromosome aberration test using human peripheral blood lymphocytes (HPBL) in both the absence and presence of an induced metabolic activation system (the 9000 g supernatant [S9] microsomal fraction of liver homogenate from rats exposed to phenobarbital/5,6-benzoflavone). Clastogenicity was evaluated by microscopic examination of HPBL in metaphase to determine the percentage of metaphase cells with numerical and/or structural chromosome aberrations.

The study was conducted in 2 phases, with a preliminary toxicity test used to determine the appropriate concentrations for the definitive chromosomal aberration assay. Water was used as a negative (vehicle) control. In both phases, the cells were treated for 3 and 21 hours in the absence of S9 mix and for 3 hours in the presence of S9 mix. The mitotic index was assessed for all cultures to determine cytotoxicity. Ten concentrations, ranging from 2.62 to 260.16 µg/mL, were evaluated in the preliminary toxicity test. Toxicity was not observed at any dose in any of the three treatment conditions. Based on these results, the highest concentration for the definitive chromosomal aberration assay was based on the limit concentration (260.16 µg/mL, 1 mM) for this test system, where relatively no cytotoxicity was observed. (S)-Norketamine concentrations of 93.66, 156.10 or 260.16 µg/mL were selected for metaphase analysis.

(S)-Norketamine caused no statistically significant increases in the proportion of metaphase figures containing chromosomal aberrations, at any analyzed concentration, when compared with the vehicle control. All mean values for the vehicle control (water), and all (S)-norketamine treatment concentrations were below to the laboratory historical control range, when taken at the upper 95% control limit.

No statistically significant increases in the proportion of polyploid or endoreduplicated metaphase cells were observed during metaphase analysis, under any treatment condition, when compared with the vehicle control whereas both positive control compounds, mytomycin C and cyclophosphamide, caused statistically significant increases in the proportion of aberrant cells, demonstrating the sensitivity of the test system and the efficacy of the S9 mix.

In conclusion, the results of the in vitro mammalian chromosome aberration test using human peripheral blood lymphocytes indicate that (S)-norketamine has shown no evidence of causing an increase in the frequency of structural chromosome aberrations with or without S9. Therefore, under the conditions of this experiment, (S)-norketamine was non-clastogenic, or negative for the induction of structural and numerical chromosomal aberrations.

Example 2: In Vivo Single Cell Gel Electrophoresis Assay and Mammalian Erythrocyte Micronucleus Test of Esketamine in Sprague Dawley Rats The potential of esketamine to induce DNA strand breaks in the liver and also assess the potential induction of micronuclei in the bone marrow cells of Crl:CD(SD) rats. Animals were treated with esketamine orally on three occasions, the second dose being administered approximately 24 hours after the first dose, with the third dose being administered approximately 21 hours after the second dose, 3 hours before sampling. All animals were dosed orally by gavage using a dose volume of 10 mL/kg.

Substantial differences in toxicity were observed between the sexes in the preliminary toxicity test, therefore, in line with current guidelines the test was performed using both male and female animals. Dose levels of 18.75, 37.5 and 75 mg/kg/day (male animals) and 12.5, 25 and 50 mg/kg/day (female animals) were selected. The vehicle control group received purified water and the positive control group for the comet phase received Ethyl Methanesulfonate at 200 mg/kg. Blood samples were taken via the tail vein on Day 3 prior to dosing, at 30 minutes and 3 hours post dose from satellite animals and all main study animals prior to termination.

Cell suspensions from each tissue were obtained from animals in the vehicle control group and in each of the test item groups approximately 3 hours after administration of the third dose. Cell suspensions from animals in the positive control group were obtained approximately 3 hours after a single dose.

Following electrophoresis three slides per animal per tissue were analyzed for comets. Slides were visualized by staining with SYBR GOLD® via fluorescence microscopy. 150 morphologically normal cells were analyzed for the presence of comets per animal per tissue. DNA strand breaks were assessed by comparing the mean and median % tail intensities (% TI) from esketamine treated animals compared to vehicle control values. The slides were also examined for any overt toxicity, e.g. an increase in background debris and/or an increase in the incidence of excessively damaged cells (i.e. Hedgehog cells). These cells were excluded from the analysis, along with any cells that had unusual staining artefacts.

Bone marrow smears were obtained from animals in the vehicle control and in each of the test item groups approximately 3 hours after administration of the third dose. In addition, slides prepared from a separate study [CT12GD] from animals treated with Cyclophosphamide a well characterized clastogen, were evaluated and coded along with the bone marrow smears prepared from animals in this study.

One smear from each animal was examined for the presence of micronuclei in 4000 polychromatic erythrocytes. The proportion of polychromatic erythrocytes was assessed by examination of at least 1000 erythrocytes from each animal. A record of the incidence of micronucleated normochromatic erythrocytes was also kept.

Statistically significant increases in the median % (TI) were observed in the liver of male Crl:CD(SD) rats administered esketamine at 75 mg/kg/day ($p<0.001$) compared to vehicle control values. The group mean and median % TI values for male animals administered esketamine at 75 mg/kg/day were outside of the current vehicle historical control range. Statistically significant increases in the median % TI were observed in the liver of female Crl:CD(SD) rats administered esketamine at 25 and 50 mg/kg/day ($p<0.001$) compared to vehicle control values. The group mean and median % TI values for female animals administered esketamine at 25 and 50 mg/kg/day were outside of the current vehicle historical control range.

The positive control compound, Ethyl methanesulphonate, produced significant increases in the median % TI when compared to vehicle control values in male and female animals ($p<0.001$, t-test). No Hedgehog cells were observed in the liver of male or female Crl:CD(SD) rats administered esketamine at any dose level, compared to vehicle control values.

Sections of the liver from the vehicle control animals and animals administered esketamine at 75 mg/kg/day (male animals) and 25 and 50 mg/kg/day (female animals) were processed for histopathological examination and assessed for signs of cytotoxicity, necrosis and apoptosis. Increased hepatocellular mitotic figures were observed some males animals given 75 mg/kg/day. The macroscopic examination performed after 3 doses of treatment revealed no test item related lesions.

No statistically significant increases in the frequency of micronucleated polychromatic erythrocytes were observed in male Crl:CD(SD) rats administered esketamine at any dose level compared to vehicle control values. All individual and group mean values were within the current vehicle historical control range (control limits).

Statistically significant decreases in the proportion of polychromatic erythrocytes were observed in male Crl:CD (SD) rats administered esketamine at 37.5 mg/kg/day (pairwise and trend test, p<0.05) and 75 mg/kg/day (trend test, p<0.05), compared to vehicle control values. All individual and group mean values were within the current vehicle historical control range (control limits); therefore this result is not considered to be biologically relevant.

No statistically significant increases in the frequency of micronucleated polychromatic erythrocytes and no statistically significant decreases in the proportion of polychromatic erythrocytes were observed in female Crl:CD(SD) rats administered esketamine at any dose level, compared to vehicle control values. All individual and group mean values were within the current vehicle historical control range (control limits). In accordance with ICH S2(R1) the coded positive control slides prepared from the study CT12GD demonstrated the ability of the scorer to detect increases in micronucleated polychromatic erythrocytes.

The results of the study indicate that esketamine has shown evidence of causing an increase in DNA strand breaks in the liver of male and female Crl:CD(SD) rats when administered orally by gavage but has not shown any evidence of causing an increase in the induction of micronucleated polychromatic erythrocytes or bone marrow cell toxicity in male or female Crl:CD(SD) rats when administered orally by gavage.

Using PROAST v63.3 (in development), the benchmark dose (BMD50) was modelled based on the mean and median tail intensity values respectively, for the male and female rats following exposure to esketamine. The Hill and exponential models provided a suitable fit to the in vivo comet tail intensity data, which is consistent with the non-linear dose response. The lower benchmark dose (BMDL50) metrics were calculated to be 9.83 mg/kg/day in female rats and 27.31 mg/kg/day in male rats, both using the 'single slide median Tail Intensity' which were lower and more conservative than those derived when using the 'single slide mean Tail Intensity'. These point of departure (POD) metrics are comparable to the no observed genotoxic effect level for comet tail intensity in liver at 12.5 mg/kg/day for female and 37.50 mg/kg/day for male rats.

Example 3: Repeated Dose 28 Day Toxicokinetic Study of Esketamine in Sprague Dawley Rats The objective of the study was to assess the potential toxicity, neurobehavioral effects, and toxicokinetics (TK) of esketamine when administered orally, via gavage, to Sprague Dawley rats for 28 days and to evaluate recovery during a 14-day drug-free period. Fifty male and 50 female rats were randomized into 4 groups (15/sex/Groups 1 and 4; 10/sex/Groups 2 and 3). Esketamine was administered via oral gavage once daily for 28 consecutive days to males at 0 (vehicle control), 6, 10 or 30 mg/kg/day and females at 0 (vehicle control), 2, 10 or 20 mg/kg/day in a dose volume of 10 mL/kg. Animals were observed until euthanized and necropsied on Day 29 (10/sex/group) or 43 (5/sex from Groups 1 and 4). Toxicity was evaluated based on mortality, clinical observations, body weights, food consumption, ophthalmology, motor activity, functional observational battery, clinical pathology (clinical chemistry, hematology, coagulation and urinalysis), organ weights, anatomic (macroscopic or microscopic) pathology. Toxicokinetic animals (3/sex/Group 1; 6/sex/Groups 2, 3, and 4) were similarly dosed and bled on Day 1 and during Week 4 for toxicokinetic analysis.

There was no mortality found in this study and there were no esketamine-related effects on clinical signs, body weights, food consumption, ophthalmology, motor activity, functional observational battery, clinical pathology or anatomic pathology changes.

Esketamine exposure increased in a generally dose-proportional manner in males and in a slightly greater than dose-proportional manner in females over the dose ranges of 6 to 30 mg/kg/day for males and 2 to 20 mg/kg/day for females. After normalization for dose level differences, males had lower exposures than females. Exposures were similar on Day 28 compared to Day 1, with the exception of $C_{max}$ in females, which was higher on Day 28. The results of the esketamine exposure at day 1 are described in Table 1, and at day 28 in Table 2.

TABLE 1

| Sex | Esketamine dose (mg/kg) | $t_{max}$ (h) | $C_{max}$ (ng/ml) | $AUC_{0-t}$ (ng*h/ml) | $AUC_{0-inf}$ (ng*h/ml) | Dose normalized $AUC_{0-inf}$ (ng*h/ml)/ (mg/kg) | $t_{1/2}$ (h) |
|---|---|---|---|---|---|---|---|
| F | 2 | 0.17 | 67.2 | 57 | 58 | 29.0 | 0.5 |
| F | 10 | 0.17 | 294.9 | 418 | 440 | 44.0 | 0.7 |
| F | 20 | 0.17 | 671.8 | 993 | 995 | 49.8 | 0.9 |
| M | 6 | 0.17 | 108.7 | 99 | 103 | 17.2 | 0.8 |
| M | 10 | 0.17 | 179.2 | 175 | 181 | 18.1 | 0.7 |
| M | 30 | 0.17 | 296.0 | 580 | 585 | 19.5 | 1.2 |

TABLE 2

| Sex | Esketamine dose (mg/kg) | $t_{max}$ (h) | $C_{max}$ (ng/ml) | $AUC_{0-t}$ (ng*h/ml) | Dose normalized $AUC_{0-t}$ (ng*h/ml)/ (mg/kg) | $t_{1/2}$ (h) |
|---|---|---|---|---|---|---|
| F | 2 | 0.17 | 132.7 | 62 | 31.0 | NC |
| F | 10 | 0.17 | 767.9 | 514 | 51.3 | 0.4 |
| F | 20 | 0.17 | 1451.1 | 1064 | 53.2 | 0.6 |
| M | 6 | 0.17 | 113.1 | 61 | 10.2 | 0.6 |
| M | 10 | 0.17 | 211.3 | 179 | 17.9 | 0.6 |
| M | 30 | 0.5 | 398.0 | 575 | 19.2 | 1.5 |

Example 4: Long Term Carcinogenicity Study

A 104 Week carcinogenicity study of esketamine administered via oral gavage to Sprague Dawley Rats is performed to evaluate the carcinogenic potential and determine the toxicokinetics of esketamine.

As based on the International Conference on Harmonization (ICH) S1 Guidelines S1A, Guideline on the Need for Carcinogenicity Studies of Pharmaceuticals; S1B, Testing for Carcinogenicity of Pharmaceuticals; and S1C(R2), Dose Selection for Carcinogenicity Studies of Pharmaceuticals, 236 male and 236 female Sprague Dawley Rats are administered esketamine over 104 weeks at the doses of 0 (vehicle control), 6, 10 or 30 mg/kg/day for the male rats and 0 (vehicle control), 2, 10 or 20 mg/kg/day for the female rats.

The study end-points include clinical observations, body weight changes, food consumption, bioanalytical toxicokinetic analysis, and anatomic macroscopic and microscopic pathology findings.

It can thus be demonstrated that the genotoxic changes as shown in Examples 1 and 2 were not identified after 28 days administration at point of departure doses and at reduced doses, which factor in an at least 10 fold safety margin after 730 days, thereby providing a minimal safe window for chronic esketamine administration.

Example 5: 7-Day Forced Swim Test in Male Rats

Groups of, 6-7 week old, male Sprague Dawley rats were administered esketamine by intraperitoneal injection and their behavioral despair assessed by a forced swim test. The animals, in cohorts of 10, were administered either a single dose of 15 mg/kg esketamine, 7 daily doses of either 7.5 or 15 mg/kg esketamine or a vehicle control, and the test performed 30 minutes after dosing. Statistical evaluation was performed using an ordinary One-Way ANOVA, t Test and an Uncorrected Fisher's LSD comparisons test.

Continuous 7-day treatment of esketamine produced stronger antidepressant-like effect than a single acute dose at the same doses levels. Esketamine at 7.5 and 15 mg/kg, exerted a statistically significant decrease of 40% and 60% respectively in immobility time following chronic treatment, whereas the extent of the effect was less marked in acute treated rats (42% of control for 15 mg/kg). This indicates that multiple dosing is more effective than a single acute dose of the same dose level and suggests a rationale to treat depressed patients via a chronic, rather than acute, esketamine regimen.

Example 6: A Single Dose, Randomized, Open-Label, Crossover Study in Healthy Volunteers A randomized, open-label 4-way crossover study in 16 healthy male and female subjects was held wherein said subjects were placed in a randomly assigned order and administered esketamine. Each subject was assigned to 1 of 4 treatment sequences according to a randomization code such that 4 subjects were assigned to each treatment sequence. There was a wash-out period of at least 7 days between dosing periods with doses consisting of either oral or intravenous esketamine hydrochloride. The study consisted of an eligibility screening period of 28 days, 4 study periods involving administration of a single dose of esketamine hydrochloride followed by safety assessments with blood sampling for PK purposes up to 72 hours after study drug administration, discharge at 72 hours after study drug administration and a follow-up visit 7-14 days after the last PK blood sample was taken on Day 4.

Fifteen of 16 subjects completed the study. One subject (Subject 11) participated in the first treatment period only. This subject was withdrawn from the study due to an AE of mild hyperbilirubinemia and therefore did not receive the planned treatments in the 3 remaining treatment periods. Subject 11 was not included in the PK set, as presented in Table 3, which therefore included 15 subjects.

TABLE 3

| Parameter | Statistic | 20 mg oral tablet | 20 mg oral solution | 100 mg oral tablet | 0.3 mg/kg iv |
|---|---|---|---|---|---|
| Esketamine | | | | | |
| $C_{max}$ (ng/ml) | Geometric mean (CV %) | 11.92 (45%) | 16.48 (48%) | 65.34 (44%) | 94.50 (33%) |
| $t_{max}$ (h) | Median | 0.75 | 0.50 | 0.75 | 1.00 |
| $AUC_{0-t}$ (ng.h/ml) | Geometric mean (CV %) | 20.05 (58%) | 23.44 (40%) | 172.71 (51%) | 249.15 (21%) |

TABLE 3-continued

| Parameter | Statistic | 20 mg oral tablet | 20 mg oral solution | 100 mg oral tablet | 0.3 mg/kg iv |
|---|---|---|---|---|---|
| $AUC_{0-inf}$ (ng.h/ml) | Geometric mean (CV %) | 22.46 (58%) | 25.82 (39%) | 180.84 (48%) | 257.14 (21%) |
| $t_{1/2}$ (h) | Geometric mean (CV %) | 2.84 (56%) | 2.91 (37%) | 7.66 (33%) | 10.16 (41%) |
| (S)-norketamine | | | | | |
| $C_{max}$ (ng/ml) | Geometric mean (CV %) | 89.73 (22%) | 99.78 (26%) | 351.89 (24%) | 42.25 (16%) |
| $t_{max}$ (h) | Median | 1.00 | 0.75 | 1.00 | 1.25 |
| $AUC_{0-t}$ (ng.h/ml) | Geometric mean (CV %) | 418.33 (22%) | 404.96 (19%) | 2267.52 (19%) | 425.96 (18%) |
| $AUC_{0-inf}$ (ng.h/ml) | Geometric mean (CV %) | 429.05 (22%) | 416.89 (19%) | 2282.91 (19%) | 440.76 (18%) |
| $t_{1/2}$ (h) | Geometric mean (CV %) | 8.75 (28%) | 8.88 (26%) | 9.27 (25%) | 11.26 (28%) |
| (2S,6S)-OH-Norketamine | | | | | |
| $C_{max}$ (ng/ml) | Geometric mean (CV %) | 45.75 (33%) | 46.46 (28%) | 189.32 (24%) | 24.79 (28%) |
| $t_{max}$ (h) | Median | 1.50 | 1.00 | 2.00 | 3.00 |
| $AUC_{0-t}$ (ng.h/ml) | Geometric mean (CV %) | 390.10 (27%) | 365.99 (32%) | 1945.85 (18%) | 376.15 (28%) |
| $AUC_{0-inf}$ (ng.h/ml) | Geometric mean (CV %) | 400.91 (26%) | 377.68 (31%) | 1959.73 (18%) | 389.50 (27%) |
| $t_{1/2}$ (h) | Geometric mean (CV %) | 7.77 (31%) | 7.83 (30%) | 8.92 (26%) | 10.68 (25%) |

Amongst the 15 subjects who completed the study, the treatment was generally well tolerated. A total of 128 TEAEs (treatment-emergent adverse event) were reported by 15 of 16 (94%) subjects of which 79 TEAEs reported by 14 of 16 (88%) subjects were to be related to the study drug. Overall, a total of 14 of 128 TEAEs reported by 4 (25%) subjects were of moderate severity and 114 of 128 TEAEs reported by 15 (94%) subjects were of mild severity. No severe TEAEs or SAEs were reported. The most frequently occurring adverse events (reported more than twice) were headache, dizziness, hypokinesia, feeling abnormal, fatigue, euphoric mood inappropriate affect, nausea and hyperhidrosis. Table 4 presents the frequency of the most frequently reported related TEAEs as a percentage of the subjects that experienced an adverse effect per treatment.

TABLE 4

| TEAE | 20 mg oral tablet/% | 20 mg oral solution/% | 100 mg oral tablet/% | 0.3 mg/kg iv/% |
|---|---|---|---|---|
| Headache | — | 19 | 13 | 19 |
| Dizziness | 13 | — | 13 | 6 |
| Hypokinesia | — | — | 13 | 6 |
| Feeling abnormal | 7 | 19 | 20 | 13 |
| Fatigue | 7 | — | — | 6 |
| Euphoric mood | — | — | 13 | 19 |
| Inappropriate affect | — | 6 | 7 | 6 |
| Nausea | — | — | 20 | 6 |
| Hyperhidrosis | 7 | — | 7 | — |

Example 7: A Safety, Tolerability, and Pharmacokinetics of Esketamine in MDD Participants Currently Treated with an Antidepressant Drug An 18 subject in patient study to assess the safety, tolerability, and pharmacokinetics of 40 mg oral esketamine in MDD participants currently treated with an antidepressant drug was held. In an, up to, 35 day screening phase, the subjects were assessed for study eligibility and, if needed, washed out from disallowed drugs. During this period, it was also determined whether the subject's current dose of oral antidepressant medication had been stable for at least 4 weeks. Eligible subjects were randomized using a 4:1 allocation scheme to receive either 40 mg oral esketamine hydrochloride or placebo once daily, respectively, for 7 days, followed by safety assessments with blood sampling for PK purposes up to 24 hours after study drug administration. Of the 15 subjects which completed the study dosed with esketamine, the mean esketamine $C_{max}$ was found to be 11.82 ng/ml and the mean esketamine $AUC_{0-t}$, 35.62 ng·h/ml.

Example 8: Oral Esketamine Dosage Forms

Oral dosage forms of esketamine hydrochloride are manufactured according to the procedures described in WO2016094358, which is incorporated in its entirety, herein, by reference.

The formulation is presented in Table 5.

TABLE 5

| Ingredient | 60 mg tablet (% (w/w)) |
| --- | --- |
| 32.0% Coated Esketamine Granules | 18.75 |
| Coated Polymer Granules | 10.04 |
| Mannitol | 33.01 |
| Crospovidone | 20.00 |
| Microcrystalline Cellulose | 13.00 |
| Carbomer | 2.00 |
| Sodium Bicarbonate | 2.00 |
| Colloidal silicon Dioxide | 0.20 |
| Magnesium stearate | 1.00 |

Example 9: A Dose Range Finding, Multicenter, Double-Randomized, Double-Blind, Placebo-Controlled Phase II Study, to Determine the Safety and Efficacy 50 mg, 65 mg and 80 mg Oral Esketamine as an Adjunctive Therapy in Major Depressive Disorder (MDD) Patients with an Inadequate Response to Standard Anti-Depressant Therapy A phase II, dose range finding, multinational, double-randomized, double-blind, placebo-controlled study compares the efficacy, safety and tolerability of once daily 50, 65 or 80 mg oral esketamine to placebo treatment in 204 MDD subjects with inadequate response to antidepressant therapy. All subjects remain on their current anti-depressant with no dose change during the study.

The study comprises 3 phases, screening (Days 0-28), double-blind treatment (days 29-56) composed of two 2-week periods (period 1, period 2) and post-treatment safety follow-up (days 57-70) following the last study treatment administration.

During screening, subjects are assessed for study eligibility and washed out from disallowed drugs. After being found eligible, subjects are randomized at the beginning of Period 1 using a 3:1:1:1 allocation scheme to receive, once daily, either placebo or 50 mg, 65 mg, or 80 mg oral esketamine, respectively. At the conclusion of period 1, all subjects are blindly assessed for response based on their change in MADRS-10 score from baseline to week 2. Subjects who received placebo during period 1 are re-randomized using a 1:1:1 allocation scheme to receive in the 2 weeks (period 2) either placebo or 50 mg, 65 mg or 80 mg oral esketamine once daily, respectively. The re-randomization is stratified by the placebo response in Period 1 (Change in MADRS < or ≥50% and MADRS score < or ≥18). Subjects that were on oral esketamine in period 1 remain on the drug at the same dosage for the 2 weeks of period 2.

Subjects receive the first dose of their study drug at the study site and are then closely monitored for 3 hours to assess for potential neuropsychiatric adverse events using a comprehensive set of scales to identify sleepiness, sedation and dissociative effects. Thereafter, the subject is provided with a 1 week supply of the study drug for administration at their place of residence and instructed to take the study drug in the evening (except at the day of the weekly visit when it is taken at the study site) and not to drive until the next morning. At every subject visit, a psychiatrist evaluates the subject's MADRS-10 score.

The study's primary efficacy endpoint is the change from baseline to week 2 (in the 2 periods) in 10 items Montgomery-Asberg Depression Rating Scale (MADRS-10).

Secondary efficacy endpoints include the change from baseline Sheehan disability scale (SDS) at 2 weeks, remission rate at 2 weeks (MADRS-10≤10), responder rate at 2 weeks (≥50% improvement in MADRS-10), change from baseline in self-rated Symptoms of Depression Questionnaire (SDQ) at 2 weeks, physician administered Clinical Global Impression Improvement (CGI-I) at 2 weeks and the change from baseline in Physician administered Clinical Global Impression Severity (CGI-S) at 2 weeks.

Exploratory Endpoints include the change from baseline in Generalized Anxiety Disorder 7 items scale (GAD-7) at 2 weeks and the change from baseline to week 4 in Montgomery-Asberg Depression Rating Scale (MADRS-10) for the subset of subjects receiving the same study drug for the 4 weeks.

Safety and tolerability endpoints include adverse events, hematology, biochemistry and urinalysis, immunological parameters, physical examination findings, blood pressure and heart rate every 30 minutes for the 3 hours following study drug administration, 12 lead ECG findings, withdrawal rates, Digit Symbol Substitution Test (DSST), reaction time test (Cambridge COGNITION), self-administered Stanford sleepiness scale, a Bladder Pain/Interstitial Cystitis Symptom Score (BPIC-SS), a Modified Observer's Alertness/Sedation Scale (MOAA/S), a Clinician-Administered Dissociative States Scale (CADSS), a suicidality scale-Clinician-Rated Columbia Suicide Severity Rating Scale (C-SSRS), 4 items positive symptoms subscale from the Brief Psychiatric Rating Scale (BPRS) and 20 item Physician Withdrawal Checklist (PWC-20) during the follow-up period.

Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

What is claimed:

1. A method of improving the Montgomery-Åsberg Depression Rating Scale (MADRS) score of a human patient suffering from major depressive disorder (MDD) and in need of treatment thereof, at at least day 28 of a treatment regimen, when compared to placebo comprising:

orally administering to said patient, once daily, at night, before the patient goes to sleep,
a dosage form comprising 60 mg of immediate-release esketamine, or a pharmaceutically acceptable salt thereof, over the treatment regimen;
wherein, more than 8 hours after the administration, the oral administration of the dosage form does not result in a mental or motor impairment that negatively affects the patient's ability to operative a motor vehicle.

2. The method of claim 1, wherein the dosage form is self-administered by the patient.

3. The method of claim 1, wherein the dosage form consists essentially of 60 mg of esketamine.

4. The method of claim 1, further comprising the administration of a second medication other than (R)-ketamine.

5. The method of claim 1, wherein prior to the administration, the human patient has not responded to adequate doses and treatment durations of antidepressants other than ketamine or esketamine.

* * * * *